United States Patent [19]
Habener

[11] Patent Number: 6,162,907
[45] Date of Patent: *Dec. 19, 2000

[54] DNA ENCODING INSULINOTROPIC HORMONE

[75] Inventor: Joel F. Habener, Newton Highlands, Mass.

[73] Assignee: The General Hospital Corporation, Boston, Mass.

[*] Notice: This patent is subject to a terminal disclaimer.

[21] Appl. No.: 09/090,949

[22] Filed: Jun. 5, 1998

Related U.S. Application Data

[63] Continuation of application No. 08/749,762, Nov. 20, 1996, Pat. No. 5,958,909, which is a continuation of application No. 08/156,800, Nov. 23, 1993, Pat. No. 5,614,492, which is a continuation of application No. 07/756,215, Sep. 5, 1991, abandoned, which is a continuation-in-part of application No. 07/532,111, Jun. 1, 1990, Pat. No. 5,118,666, which is a continuation of application No. 07/148,517, Jan. 26, 1988, abandoned, which is a continuation-in-part of application No. 06/859,928, May 5, 1986, abandoned.

[51] Int. Cl.$^7$ .......................... C07H 21/02; C07K 14/00; C07K 5/00; A61K 38/00
[52] U.S. Cl. ...................... 536/23.1; 530/350; 530/300; 530/324; 514/12
[58] Field of Search ................................ 530/300, 350, 530/324; 536/23.1

[56] References Cited

U.S. PATENT DOCUMENTS

| | | |
|---|---|---|
| 5,118,666 | 6/1992 | Habener . |
| 5,120,712 | 6/1992 | Habener . |
| 5,424,286 | 6/1995 | Eng .............................. 514/2 |
| 5,545,618 | 8/1996 | Buckley et al. .......................... 514/12 |
| 5,574,008 | 11/1996 | Johnson et al. ............................ 514/12 |
| 5,614,492 | 3/1997 | Habener . |
| 5,631,224 | 5/1997 | Efendic et al. ............................ 514/12 |
| 5,958,909 | 9/1999 | Habener . |

FOREIGN PATENT DOCUMENTS

| | | |
|---|---|---|
| 0 044 168 A1 | 1/1982 | European Pat. Off. . |
| 0 082 731 A1 | 6/1983 | European Pat. Off. . |
| 0 619 322 A2 | 10/1994 | European Pat. Off. . |
| 0 658 568 A1 | 6/1995 | European Pat. Off. . |
| 0 305 387 B2 | 8/1996 | European Pat. Off. . |
| 0 733 644 A1 | 9/1996 | European Pat. Off. . |
| 2 732 894 | 10/1996 | France . |
| 19530865 A1 | 2/1997 | Germany . |
| 1-502746 | 9/1989 | Japan . |
| 2583257 | 2/1997 | Japan . |
| WO 90/11296 | 10/1990 | WIPO . |
| WO 91/11457 | 8/1991 | WIPO . |
| WO 93/18785 | 9/1993 | WIPO . |
| WO 93/19175 | 9/1993 | WIPO . |
| WO 93/25579 | 12/1993 | WIPO . |
| 95/03405 | 2/1995 | WIPO . |
| WO 95/05848 | 3/1995 | WIPO . |
| WO 95/07098 | 3/1995 | WIPO . |
| WO 95/17510 | 6/1995 | WIPO . |
| WO 95/31214 | 11/1995 | WIPO . |
| WO 96/20005 | 7/1996 | WIPO . |
| 98/19698 | 5/1998 | WIPO . |

OTHER PUBLICATIONS

Albano, J.D.M., et al., "A Sensitive, Precise Radioimmunoassay of Serum Insulin Relying on Charcoal Separation of Bound and Free Hormone Moieties," *Acta Endocrinologica* 70:487–509 (1972).

Andersen, D.K., et al., "The Insulinotropic Effect of GIP: A Dose Response Comparison and Comparison to Glucagon–Like Peptide-1(7–37) amide (GLP)," *Diabetes* 39(*Suppl. 1*):142A, Abstract No. 567 (May 1990).

Andrews, P.C. and Ronner, P., "Isolation and Structures of Glucagon and Glucagon–like Peptide from Catfish Pancreas," *J. Biol. Chem.* 260(7):3910–3914 (Apr. 1985).

Bell, G.I., et al., "Hamster preproglucagon contains the sequence of glucagon and two related peptides," *Nature* 302:716–718 (1983).

Blackmore, P.F., et al., "Absence of insulinotropic glucagon–like peptide–1(7–37) receptors on isolated rat liver hepatocytes," *FEBS Lett.* 283(1):7–10 (May 1991).

Creutzfeldt, W., et al., "Entero–Insular Axis 1988," in *Diabetes 1988*, Larkins, R. et al., eds., Elsevier Science Publishers B.V. (Biomedical Division), pp. 193–203 (1989).

Dobbs, R., et al., "Glucagon: Role in the Hyperglycemia of Diabetes Mellitus," *Science* 187:544–547 (1975).

Dobs, A.S., et al., "Regulation of Insulin Synthesis in an Insulin–Producing Cell Line (RINm5F): Long–Term Experiments," *In Vitro Cell. Dev. Biol.* 25(2):112–114 (Feb. 1989).

Drucker, D.J., et al., "Cell–specific Post–translational Processing of Preproglucagon Expressed from a Metallothionein–glucagon Fusion Gene," *J. Biol. Chem.* 261(21):9637–9643 (1986).

Drucker, D.J., et al., "Glucagon–like Peptide I Increases Insulin mRNA Levels and Insulin Release in Rat Insulinoma Cells," Abstract No. 602, Programs and Abstracts book, 68$^{th}$ Annual Meeting of The Endocrine Society, Jun. 25–27, 1986, Anaheim, CA (Jun. 1986).

Drucker, D.J., et al., "Glucagon–like peptide I stimulates insulin gene expression and increases cyclic AMP levels in a rat islet cell line," *Proc. Natl. Acad. Sci. USA* 84:3434–3438 (May 1987).

Fehmann, H.C., et al., "Functional receptors for the insulinotropic hormone glucagon–like peptide–I(7–37) on a somatostatin secreting cell line," *FEBS Lett.* 279(2):335–340 (Feb. 1991).

Fehmann, H.C., et al., "Insulinotropic Hormone Glucagon–like Peptide–I(7–37) Stimulation of Proinsulin Gene Expression and Proinsulin Biosynthesis in Insulinoma βTC–1 Cells," *Endocrinology* 130(1):159–166 (1992).

(List continued on next page.)

*Primary Examiner*—Nita Minnifield
*Attorney, Agent, or Firm*—Sterne, Kessler, Goldstein & Fox P.L.L.C.

[57] ABSTRACT

Derivatives of glucagon-like peptide I (GLP-1) and especially GLP-1(7-36) have been found to have insulinotropic activity. The invention pertains to the use of GLP-1(7-36) for the treatment of type II diabetes mellitus.

2 Claims, 17 Drawing Sheets

OTHER PUBLICATIONS

Ganong, W.F., "Endocrine Functions of the Pancreas & the Regulation of Carbohydrate Metabolism," in *Review of Medical Physiology*, LANGE Medical Publications, Los Altos, CA, pp. 257–276 (1979).

Garcia, S.D., et al., "Biosynthesis of Proinsulin and Insulin in Newborn Rat Pancreas," *J. Clin. Invest.* 57:230–243 (1976).

Gefel, D., et al., "Glucagon–Like Peptide–I Analogs: Effects on Insulin Secretion and Adenosine 3',5'–Monophosphate Formation," *Endocrinology* 126(4):2164–2168 (1990).

George, S.K., et al., "Molecular forms of glucagon–like peptides in man," *FEBS Lett.* 192(2):275–278 (Nov. 1985).

German, M.S., et al., "Regulation of Insulin Gene Expression by Glucose and Calcium in Transfected Primary Islet Cultures," *J. Biol. Chem.* 265(36):22063–22066 (Dec. 1990).

Ghiglione, M., et al., "How glucagon–like is glucagon–like peptide–1?," *Diabetologia* 27:599–600 (1984).

Ghiglione, M., et al., "Plasma Responses of Glucagon–Like Peptide–1 and –2 Immunoreactivities to Oral Glucose in Man," *Reg. Peptides* 13:101 (Dec. 1985).

Grodsky, G.M., et al., "Pancreatic action of the sulfonylureas," *Fed. Proc.* 36(13):2714–2719 (1977).

Habener, J.F., et al., "Complementary DNAs Encoding Precursors of Glucagon and Somatostatin," in: *Biogenetics of Neurohormonal Peptides*, Håkanson, R., et al. eds., Academic Press, London, pp. 47–61 (1985).

Habener, J.F., et al., "Cell–Specific Alternative Processing of Proglucagon," in Molecular Mechanisms in Secretion. Alfred Benzon Symposium 25, Thorn, N.A. et al., eds., Munksgaard, Copenhagen, pp. 476–492 (1988).

Habener, J.F., "Cyclic AMP Response Element Binding Proteins: A Cornucopia of Transcription Factors," *Molec. Endo.* 4(8):1087–1094 (1990).

Hammonds, P., et al., "Glucose regulates preproinsulin messenger RNA levels in a clonal cell line of simian virus 40–transformed B cells," *FEBS Lett.* 213(1):149–154 (Mar. 1987).

Hammonds, P., et al., "Regulation and specificity of glucose–stimulated insulin gene expression in human islets of Langerhans," *FEBS Lett.* 223(1):131–137 (Oct. 1987).

*Harrison's Principles of Internal Medicine*, 11th Ed., Braunwald, E. et al., eds., McGraw–Hill Book Company, New York, NY, p. 1782 (1987).

Hauner, H., et al., "Effects of Gastric Inhibitory Polypeptide on Glucose and Lipid Metabolism of Isolated Rat Adipocytes," *Ann. Nutr. Metab.* 32:282–288 (1988).

Hausdorff, W.P., et al., "Turning off the signal: desensitization of β–adrenergic receptor function," *FASEB J.* 4:2881–2889 (Aug. 1990).

Heinrich, G., et al., "Pre–Proglucagon Messenger Ribonucleic Acid: Nucleotide and Encoded Amino Acid Sequences of the Rat Pancreatic Complementary Deoxyribonucleic Acid," *Endocrinology* 115(6):2176–2181 (1984).

Hendrick, G., et al., "Glucagon–Like Peptide I–(7–37) [GLP] Enhances Glucose Disposal In Vivo," *Diabetes* 39(*Suppl. 1*):260A, Abstract No. 1005 (May 1990).

Hendrick, G.K., et al., "Glucagon–like Peptide–I–(7–37) Suppresses Hyperglycemia in Rats," *Metabolism* 42(1):1–6 (1993).

Holst, J.J., et al., "Truncated glucagon–like peptide I, an insulin–releasing hormone from the distal gut," *FEBS Lett.* 211(2):169–174 (Jan. 1987).

Hoosein, N.M. and Gurd, R.S., "Human glucagon–like peptides 1 and 2 activate rat brain adenylate cyclase," *FEBS Lett.* 178(1):83–86 (1984).

Houghten, R.A., et al., "Simultaneous Multiple Peptide Synthesis: The Rapid Preparation of Large Numbers of Discrete Peptides for Biological, Immunological, and Methodological Studies," *BioTechniques* 46(6):522–528 (1986).

Jones, I.R., et al., "The effects of glucose–dependent insulinotropic polypeptide infused at physiological concentrations in normal subjects and Type 2 (non–insulin–dependent) diabetic patients on glucose tolerance and B–cell secretion," *Diabetologia* 30:707–712 (1987).

Komatsu, R., et al., "Effect of Glucogon–Related Peptides on Rat Endocrine Pancreas," *Biomed. Res.* 9(*Suppl. 3*):201–206 (1988).

Korman, L.Y., et al., "Characteristics of the Interaction of the Glucagon Receptor, cAMP, and Insulin Secretion in Parent Cells and Clone 5F of a Cultured Rat Insulinoma," *Diabetes* 34:717–721 (Aug. 1985).

Kreymann, B., et al., "Glucagon–Like Peptide–1 7–36: A Physiological Incretin in Man," *Lancet* pp. 1300–1304, Dec. 5, 1987.

Lee, C.Q., et al., "Cyclic–AMP–responsive transcriptional activation of CREB–327 involves interdependent phosphorylated subdomains," *EMBO J.* 9(13):4455–4465 (1990).

Lentz, K.E., et al., "The Amino Acid Composition of Hypertensin II and Its Biochemical Relationship to Hypertensin I," *J. Exp. Med.* 104:183–191 (1956).

Levy, J. and Malaisse, W.J., "The Stimulus–Secretion Coupling of Glucose–Induced Insulin Release–XVII," *Biochem. Pharm.* 24:235–239 (1975).

Lopez, L.C., et al., "Mammalian pancreatic preproglucagon contains three glucagon–related peptides," *Proc. Natl. Acad. Sci. USA* 80:5485–5489 (1983).

Lund, P.K., et al., "Pancratic preproglucagon cDNA contains two glucagon–related coding sequences arranged in tandem," *Proc. Natl. Acad. Sci. USA* 79:345–349 (1982).

Meienhofer, J., "Large Scale Peptide Synthesis: A Review," in Peptides 1984. Proceedings of the 18th European Peptide Symposium, Ragnarsson, U., ed., Almqvist & Wiksell International, Stockholm, Sweden, pp. 19–34 (1984).

Minamitake, Y., et al., "Syntheses and Biological Activities of α–Human Atrial Natriuretic Polypeptide and Its Analogs," in *Peptide Chemistry 1984*, N. Izumiya, Ed., Protein Research Foundation, Osaka, Japan, pp. 229–234 (1985).

Mojsov, S., et al., "Preproglucagon Gene Expression in Pancreas and Intestine Diversifies at the Level of Post–translational Processing," *J. Biol. Chem.* 261(25):11880–11889 (Sep. 1986).

Mojsov, S., et al., "Insulinotropin: Glucagon–like Peptide I (7–37) Co–encoded in the Glucagon Gene Is a Potent Stimulator of Insulin Release in the Perfused Rat Pancreas," *J. Clin. Invest.* 79(2):616–619 (1987).

Mojsov, S., et al., "Both Amidated and Nonamidated Forms of Glucagon–like Peptide I Are Synthesized in the Rat Intestine and the Pancreas," *J. Biol. Chem.* 265(14):8001–8008 (1990).

Moody, A.J., et al., "Relationship of glicentin to proglucagon and glucagon in the porcine pancreas," *Nature* 289:514–516 (1981).

Morris, G.E. and Korner, A., "The Effect of Glucose on Insulin Biosynthesis by Isolated Islets of Langerhans of the Rat," *Biochim. Biophys. Acta* 208:404–413 (1970).

Nathan, D.M., et al., "Insulinotropic Action of Glucagon–like Peptide–I,7–37[GLP–I(7–37)] in Non–Diabetic and NIDDM Subjects," *Diabetes* 39(*Suppl. 1*):142A, Abstract No. 568 (May 1990).

Nielsen, D.A., et al., "Control of Insulin Gene Expression in Pancreatic β–Cells and in an Insulin–producing Cell Line, RIN–5F Cells," *J. Biol. Chem.* 260(25):13585–13589 (Nov. 1985).

Ørskov, C., et al., "Glucagon–Like Peptides GLP–1 and GLP–2, Predicted Products of the Glucagon Gene, Are Secreted Separately from Pig Small Intestine but Not Pancreas," *Endocrinology* 119(4):1467–1475 (1986).

Ørskov, C., et al., "Proglucagon Products in Plasma of Noninsulin–dependent Diabetics and Nondiabetic Controls in the Fasting State and after Oral Glucose and Intravenous Arginine," *J. Clin. Invest.* 87:415–423 (Feb. 1991).

Ørskov, C., et al., "Biological Effects and Metabolic Rates of Glucagonlike Peptide–1 7–36 Amide and Glucagonlike Peptide–1 7–37 in Healthy Subjects Are Indistinguishable," *Diabetes* 42:658–661 (1993).

Patzelt, C., et al., "Identification and processing of proglucagon in pancreatic islets," *Nature* 282:260–266 (1979).

Patzelt, C. and Schiltz, E., "Conversion of proglucagon in pancreatic alpha cells: The major endproducts are glucagon and a single peptide, the major proglucagon fragment, that contains two glucagon–like sequences," *Proc. Natl. Acad. Sci. USA* 81:5007–5011 (1984).

Philippe, J. and Missotten, M., "Functional Characterization of a cAMP–responsive Element of the Rat Insulin I Gene," *J. Biol. Chem.* 265(3):1465–1469 (Jan. 1990).

Rudinger, J., "Characteristics of the amino acids as components of a peptide hormone sequence," in *Peptide Hormones*, Parsons, J.A., ed., Univ. Park Press, Baltimore, MD, pp. 1–7 (1976).

Sarson, D.L., et al., "The Effect of Glucose–Dependent Insulinotropic Polypeptide Infused at Physiological Concentrations on the Release of Insulin in Man," *Diabetologia* 22:33–36 (1982).

Schäfer, R. and Schatz, H., "Stimulation of (Pro–)Insulin Biosynthesis and Release by Gastric Inhibitory Polypeptide in Isolated Islets of Rat Pancreas," *Acta Endo.* 91:493–500 (1979).

Schatz, H., et al., "The Effect of Tolbutamide and Glibenclamide on the Incorporation of [$^3$H]Leucine and on the Conversion of Proinsulin to Insulin in Isolated Pancreatic Islets," *FEBS Lett.* 26(1):237–240 (1972).

Schmidt, W.E., et al., "Glucagon–like peptide–1 but not glucagon–like peptide–2 stimulates insulin release from isolated rat pancreatic islets," *Diabetologia* 28(9):704–707 (Sep. 1985).

Schwartz, T.W., "The processing of peptide precursors. 'Proline–directed arginyl cleavage' and other monobasic processing mechanisms," *FEBS Lett.* 200(1):1–10 (May 1986).

Shields, D., et al., "Cell–free synthesis and processing of multiple precursors to glucagon," *Nature* 289(5797):511–514 (1981).

Stephen, R.L., et al., "Potential novel methods for insulin admimistration: I. Iontophoresis," *Biomed. Biochim. Acta* 43(5):553–558 (1984).

Tanese, T., et al., "Synthesis and Release of Proinsulin and Insulin by Isolated Rat Islets of Langerhans," *J. Clin. Inves.* 49:1394–1404 (1970).

Unger, R.H. and Orci, L., "Glucagon in Diabetes Mellitus," in *Glucagon II*, Lefébvre, P.J., ed., Springer–Verlag, Berlin, Germany, pp. 431–450 (1983).

Uttenthal, L.O., et al., "Molecular Forms of Glucagon–Like Peptide–1 in Human Pancreas and Glucagonomas," *J. Clin. Endo. Metab.* 61(3):472–479 (Sep. 1985).

Wang, S.–Z., et al., "Agonist–induced down–regulation of m1 muscarinic receptors and reduction of their mRNA level in a transfected cell line," *FEBS Lett.* 276(1.2):185–188 (Dec. 1990).

Weir, G.C., et al., "Glucagonlike Peptide 1 (7–37) Actions on Endocrine Pancreas," *Diabetes* 38:338–342 (Mar. 1989).

Welsh, M., et al., "Control of Insulin Gene Expression in Pancreatic β–Cells and in an Insulin–producing Cell Line, RIN–5F Cells. II. Regulation of Insulin mRNA Stability," *J. Biol. Chem.* 260(25):13590–13594 (Nov. 1985).

Yanaihara, C., et al., "Rat pancreas contains the proglucagon(64–69) fragment and arginine stimulates its release," *FEBS Lett.* 187(2):307–310 (Aug. 1985).

Certificate of Correction for U.S. Patent No. 5,120,712.

NIH Grant No. R29 DK40083 to Svetlana Mojsov entitled "Role of GLP–I(7–37) in Insulin Secretion," beginning Apr. 1, 1988.

NIH Crisp Printout of Abstract for AM30834–01, Fiscal Year 1982, "Glucagon biosynthesis and metabolism (fish, rats).".

NIH Crisp Printout of Abstract for AM30834–02, Fiscal Year 1983, "Glucagon biosynthesis and metabolism (fish, rats).".

NIH Crisp Printout of Abstract for AM30834–03, Fiscal Year 1984, "Glucagon biosynthesis and metabolism (fish, rats).".

NIH Crisp Printout of Abstract for AM30834–04, Fiscal Year 1985, "Glucagon biosynthesis and metabolism (fish, rats).".

NIH Crisp Printout of Abstract for AM30834–05, Fiscal Year 1986, "Glucagon biosynthesis and metabolism (fish, rats).".

NIH Crisp Printout of Abstract for DK30834–05S1, Fiscal Year 1987, "Glucagon biosynthesis and metabolism (fish, rats).".

NIH Crisp Printout of Abstract for DK30834–06A1, Fiscal Year 1988, "Glucagon biosynthesis and metabolism (human, rats, hamsters).".

NIH Crisp Printout of Abstract for DK30834–07, Fiscal Year 1989, "Glucagon biosynthesis and metabolism (human, rats, hamsters).".

NIH Crisp Printout of Abstract for DK30834–08, Fiscal Year 1990, "Glucagon bioysynthesis and metabolism (human, rats, hamsters).".

NIH Crisp Printout of Abstract for DK30834–09, Fiscal Year 1991, "Glucagon biosynthesis and metabolism (human, rats, hamsters).".

English Language Abstract of FR 2 732 894 , Derwent World Patents Index (Dialog File 351), WPI Accession No. 96–479332.

English Language Abstract of DE 195 30 865, Derwent World Patents Index (Dialog File 351), WPI Accession No. 97–146440.

English Language Abstract of JP 1–502746, Derwent World Patents Index (Dialog File 351), WPI Accession No. 87–334950.

English Language Abstract of JP 2583257, Derwent World Patents Index (Dialog File 351), WPI Accession No. 87–334950.

Entry entitled "angiotensin," in *Seikagaku Jiten* (Biochemical Dictionary), First edition, Tokyo Kagaku Dojin, pp. 97–98 (1985).
Entry entitled "diabetes mellitus," in *Seikagaku Jiten* (Biochemical Dictionary), First edition, Tokyo Kagaku Dojin, pp. 868 (1985).

Buhl et al, JBC, 1988, 263/18:8621–8624.
Orskov et al, JBC, 264/22:12326–29, 1989.
Holz et al, JBC, 274/20:14147–14156, 1999.
Fehmann et al, Endocrinology, 130/5:2890–2896, 1992.
Fehmann et al, Trends on Endocrinol, 3:158–163, 1992.
Bromer et al, JBC, 246:2822–2827, 1974.

```
5'
aaaggagctccacctgtctacacctcctctcagctcagtcccacaaggcagaataaaaaaa
                                                        -20
                                                  Met Lys Thr Val Tyr    75
                                                  ATG AAG ACC GTT TAC
├─────── SIGNAL PEPTIDE ───────┤ -1 +1
Ile Val Ala Gly Leu Phe Val Met Leu Val Gln Gly Ser Trp Gln His Ala Pro Gln Asp   135
ATC GTG GCT GGA TTG TTT GTA ATG CTG GTA CAA GGC AGC TGG CAG CAT GCC CCT CAG GAC
                          ├──── NH₂-PEPTIDE ────
                                                                           25
Thr Glu Glu Asn Ala Arg Ser Phe Pro Ala Ser Gln Thr Glu Pro Leu Glu Asp Pro Asp   195
ACG GAG GAG AAC GCC AGA TCA TTC CCA GCT TCA CAG ACA GAA CCA CTT GAA GAC CCT GAT
                                                                           45
Gln Ile Asn Glu Asp Lys Arg His Ser Gln Gly Thr Phe Thr Ser Asp Tyr Ser Lys Tyr   255
CAG ATA AAC GAA GAC AAA CGC CAT TCA CAG GGC ACA TTC ACC AGT GAC TAC AGC AAA TAC
                      ├───────────────── GLUCAGON ─────────────────
                                                                           65
Leu Asp Ser Arg Arg Ala Gln Asp Phe Val Gln Trp Leu Met Asn Thr Lys Arg Asn Arg   315
CTA GAC TCC CGC CGT GCT CAA GAT TTT GTG CAG TGG TTG ATG AAC ACC AAG AGG AAC CGG
├── IP-I ──┤                                                       ├── GLP I ──
                                                                           85
Asn Asn Ile Ala Lys Arg His Asp Glu Phe Glu Arg His Ala Glu Gly Thr Phe Thr Ser   375
AAC AAC ATT GCC AAA AGA CAT GAT GAA TTT GAG AGG CAT GCT GAA GGG ACC TTT ACC AGT
                                                                           105
Asp Val Ser Ser Tyr Leu Glu Gly Gln Ala Ala Lys Glu Phe Ile Ala Trp Leu Val Lys   435
GAT GTG AGT TCT TAC TTG GAG GGC CAG GCA GCA AAG GAA TTC ATT GCT TGG CTG GTG AAA
                                                      ├─────── IP-II ───────
                                                                           125
Gly Arg Gly Arg Arg Asp Phe Pro Glu Val Ala Ile Ala Glu Glu Leu Gly Arg Arg       495
GGC CGA GGA AGG CGA GAC TTC CCG GAA GTC GCC ATA GCT GAG GAA CTT GGG CGC AGA
```

FIG. 1

```
                                                                    ┌─────────────────────────────────────────────────────── GLP II ──
His Ala Asp Gly Ser Phe Ser Asp Glu Met Asn Thr Ile Leu Asp Asn Ala Thr Arg
CAT GCT GAT GGA TCC TTC TCT GAT GAG ATG AAC ACG ATT CTC GAT AAC GCC ACC AGA    555
                                                        155
Asp Phe Ile Asn Trp Leu Ile Gln Thr Lys Ile Thr Asp (Lys)(Lys) End
GAC TTC ATC AAC TGG CTG ATT CAA ACC AAG ATC ACT GAC  AAG  AAA  TAG gaatatttcaccatt    618 cacaaccatcttcacaacatctcctgccagtcacttggatgtacatttgagagcatatccgaagctatactgcttttgc       697 atgcggacgaatacatttcccttttagcgttgtgtaaccaaaggttgtaaatgaataaagtttttccagggtgtgttgat      776 aaagtaacaactttacagtatgaaaatgctggattctcaaattgtctcctcgtttgaagttaccgccctgagattact        855 tttctgtggtataaattgtaaattatcgcagtcacgacaccggattacaacagaagacatggtaacctggtaacc           933 gtagtggtgaacctggaaagagaacttcttccttgaacccctttgtcataaatgcgctcagctttcaatgtatcaagaat      1012 agatttaaaatatatctcat                                                                  1024
        3'
```

*FIG. 1 CONT.*

DNA ENCODING INSULINOTROPIC HORMONE

CROSS-REFERENCE TO RELATED APPLICATIONS

This application is a continuation of U.S. application Ser. No. 08/749,762, filed Nov. 20, 1996 U.S. Pat. No. 5,958,909, which is a continuation of U.S. application Ser. No. 08/156,800, filed Nov. 23, 1993, now U.S. Pat. No. 5,614,492, which is a file wrapper continuation of U.S. application Ser. No. 07/756,215, filed Sep. 5, 1991, now abandoned, which is a continuation-in-part of U.S. application Ser. No. 07/532,111, filed Jun. 1, 1990, now U.S. Pat. No. 5, 118,666 which is a file wrapper continuation of U.S. application Ser. No. 07/148,517, filed Jan. 26, 1988, now abandoned which is a continuation-in-part of U.S. application Ser. No. 06/859,928, filed on May 5, 1986 and now abandoned.

BACKGROUND OF THE INVENTION

1. Field of the Invention

This invention is directed to the discovery that certain peptide fragments of the prohormone, proglucagon, possess hormonal activities and can be used to stimulate the synthesis and secretion of the hormone, insulin. These peptide fragments are useful in therapy and treatment of maturity onset (type II) diabetes mellitus. This invention is specifically directed to the use of glucagon-like peptide-1(7-36) for the treatment of maturity onset diabetes mellitus, and for use as an insulin secretagague per se.

2. Description of the Background Art

The endocrine secretions of the pancreatic islets are under complex control not only by blood-borne metabolites (glucose, amino acids, catecholamines, etc.), but also by hormonal and local paracrine influences. The major pancreatic islet hormones (glucagon, insulin, and somatostatin) interact among their specific cell types (A, B, and D cells, respectively) to modulate secretory responses mediated by the metabolites. Although insulin secretion is predominantly controlled by blood levels of glucose, glucagon and somatostatin stimulate and inhibit glucose-mediated insulin secretory responses, respectively. In addition to the proposed interislet paracrine regulation of insulin secretion, there is evidence to support the existence of insulinotropic factors in the intestine. This concept originates from the observations that glucose taken orally is a much more potent stimulant of insulin secretion than is a comparable amount of glucose given intravenously.

The human hormone, glucagon, is a 29-amino acid peptide hormone produced in the A-cells of the pancreas. The hormone belongs to a multi-gene family of structurally related peptides that include secretin, gastric inhibitory peptide, vasoactive intestinal peptide, and growth hormone-releasing hormone. These peptides variously regulate carbohydrate metabolism, gastrointestinal mobility, and secretory processes. The principal recognized actions of pancreatic glucagon, however, are to promote hepatic glycogenolysis and gluconeogenesis, resulting in an elevation of blood sugar levels. In this regard, the actions of glucagon are counterregulatory to those of insulin and may contribute to the hyperglycemia that accompanies diabetes mellitus (Dobbs, R., et al., *Science* 187:544–547 (1975)).

In supraphysiologic concentrations, glucagon has been found to be capable of binding to receptors which lie on the surface of insulin-producing cells. Glucagon, when bound to these receptors, stimulates the rapid synthesis of cAMP by these cells. cAMP, in turn, stimulates insulin expression (Korman, L. Y., et al., *Diabetes* 34:717–722 (1985)). Glucose and insulin act to inhibit glucagon synthesis (*Review of Medical Physiology*, Ganong, W. F., 1979, Lang Publications, Los Altos, Calif.(p. 273)). Thus, the expression of glucagon is down-regulated by insulin, and ultimately by the serum glucose level.

The glucagon gene is initially translated from a 630-base pair precursor to form the polypeptide, preproglucagon (Lund, P. K., et al., *Proc. Natl. Acad. Sci., USA* 79:345–349 (1982)). This polypeptide is subsequently processed to form proglucagon. Patzelt, C., et al (*Nature* 282:260–266 (1979)) demonstrated that proglucagon was subsequently cleaved into glucagon and a second polypeptide. Subsequent work by Lund, P. K., et al. (*Proc. Natl. Acad. Sci. USA* 79:345–349 (1982)); Lopez, L. C., et al. (*Proc. Natl. Acad. Sci. USA* 80:5485–5489 (1983)) and Bell, G. I., et al. (*Nature* 302:716–718 (1983)) indicated that the proglucagon molecule was cleaved immediately after lysine-arginine dipeptide residues. Studies of proglucagon produced by channel catfish (*Ictalurus punctata*) indicated that glucagon from this animal was also proteolytically cleaved after adjacent lysine-arginine and arginine-arginine dipeptide residues (Andrews, P. C., et al., *J. Biol Chem.* 260:3910–3914 (1985)). Lopez, L. C., et al. (*Proc. Natl. Acad. Sci. USA* 80:5485–5489 (1983)), and Bell, G. I., et al. (*Nature* 302:716–718 (1983)), discovered the mammalian proglucagon was cleaved at lysine-arginine or arginine-arginine dipeptides and demonstrated that the mammalian proglucagon molecule contained three discrete and highly homologous peptide molecules which were designated glucagon, glucagon-like peptide 1 (GLP-1or GLP-I), and glucagon-like peptide 2 (GLP-2 or GLP-II). Lopez et al. (*Proc. Natl. Acad. Sci. USA* 80:5485–5489 (1983)) concluded that GLP-1was 37 amino acid residues long and that GLP-2 was 34 amino acid residues long. Analogous studies on the structure of rat preproglucagon revealed a similar pattern of proteolytic cleavage between adjacent lysine-arginine or arginine-arginine dipeptide residues, resulting in the formation of glucagon, GLP-1, and GLP-2 (Heinrich, G., et al., *Endocrinol.* 115:2176–2181 (1984)). Human rat, bovine, and hamster sequences of GLP-1have been found to be identical (Ghiglione, M., et al., *Diabetologia* 27:599–600 (1984)).

The conclusion reached by Lopez et al. (*Proc. Natl. Acad. Sci. USA* 80:5485–5489 (1983)) regarding the size of GLP-1was confirmed by the work of Uttenthal, L. O., et al., (*J. Clin. Endocrinol. Metabol.* 61:472–479 (1985)). Uttenthal et al. examined the molecular forms of GLP-1which were present in the human pancreas. Their research shows that GLP-1and GLP-2 are present in the pancreas as proteins having 37 and 34 amino acid residues, respectively.

The similarity between GLP-1and glucagon suggested to early investigators that GLP-1might have biological activity. Although some investigators found that GLP-1could induce rat brain cells to synthesize cAMP (Hoosein, N. M., et al., *FEBS Lett.* 178:83–86 (1984)), other investigators failed to identify any physiological role for GLP-1(Lopez, L. C., et al., *Proc. Natl. Acad. Sci. USA* 80:5485–5489 (1983)). The failure to identify any physiological role for GLP-1caused some investigators to question whether GLP-1was in fact a hormone and whether the relatedness between glucagon and GLP-1might be artifactual (Ghiglione, M., et al., *Diabetologia* 27:599–600 (1984)).

Thus, in conclusion, the prior art reveals an awareness of the processing of a glucagon hormone precursor into a set of peptides sharing extensive homology. It has been widely assumed by those of skill in the art that these highly related glucagon-like peptides would have a biological activity. Nevertheless, extensive investigations designed to elucidate the biological effects of these molecules had been unsuccessful.

SUMMARY OF THE INVENTION

The present invention relates to an insulinotropic hormone comprising a fragment of GLP-1 and derivatives thereof, especially GLP-1(7-36). The invention additionally pertains to the therapeutic uses of such compounds, and especially to the use of GLP-1(7-36) for the treatment of maturity onset diabetes mellitus.

In detail, the invention pertains to a peptide fragment which is insulinotropic and is derivable from a naturally occurring amino acid sequence.

The invention comprises a compound selected from the group consisting of:
- (A) GLP-1(7-36) peptide comprising the sequence:
  His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg and
- (B) a derivative of such peptide;

wherein the compound is substantially free of natural contaminants, and has an insulinotropic activity which exceeds the insulinotropic activity of GLP-1(1-36) or GLP-1(1-37).

The invention also includes a compound selected from the group consisting of:
- (A) GLP-1(7-36) peptide comprising the sequence:
  His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg and
- (B) a derivative of such peptide;

wherein the compound is substantially free of natural contaminants, and has an insulinotropic activity at a concentration of at least $10^{-10}$ M.

Of particular interest are GLP-1(7-36) peptides of the following formula:
(1) $H_2N-X-CO-R^1$
  wherein $R^1$ is OH, OM, or $-NR^2R^3$;
  M is a pharmaceutically acceptable cation or a lower branched or unbranched alkyl group;
  $R^2$ and $R^3$ are the same or different and selected from the group consisting of hydrogen and a lower branched or unbranched alkyl group;
  X is a GLP-1(7-36) peptide comprising the sequence:
    His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg;
  $NH_2$ is the amine group of the amino terminus of X; and
  CO is the carbonyl group of the carboxy terminus of X and where the naturally processed form is argininea-mide at position 36 of GLP-1(7-36);
(2) the acid addition salts thereof; and
(3) the protected or partially protected derivatives thereof;

wherein such compound has an insulinotropic activity which exceeds the insulinotropic activity of GLP-1(1-36) or GLP-1(1-37).

The invention further pertains to a method for enhancing the expression of insulin which comprises providing to a mammalian pancreatic B-type islet cell an effective amount of the insulinotropic peptides disclosed above.

The invention further pertains to a method for treating maturity-onset diabetes mellitus which comprises administration of an effective amount of the insulinotropic peptides discussed above to a patient in need of such treatment.

BRIEF DESCRIPTION OF THE DRAWINGS

FIG. 1 shows the DNA structure and corresponding amino acid sequence of human, rat, and hamster preproglucagons. The preproglucagon precursor is proteolytically cleaved at sites indicated by circles.

FIGS. 9 and 10 show the plasma glucose levels and serum insulin levels in maturity onset diabetic subjects during infusion of GLP-1(7-37) either before or after lowering fasting glucose levels by the administration of overnight insulin infusion.

DESCRIPTION OF THE PREFERRED EMBODIMENTS

A. GLP-1 and Its Derivatives

Figure 2:
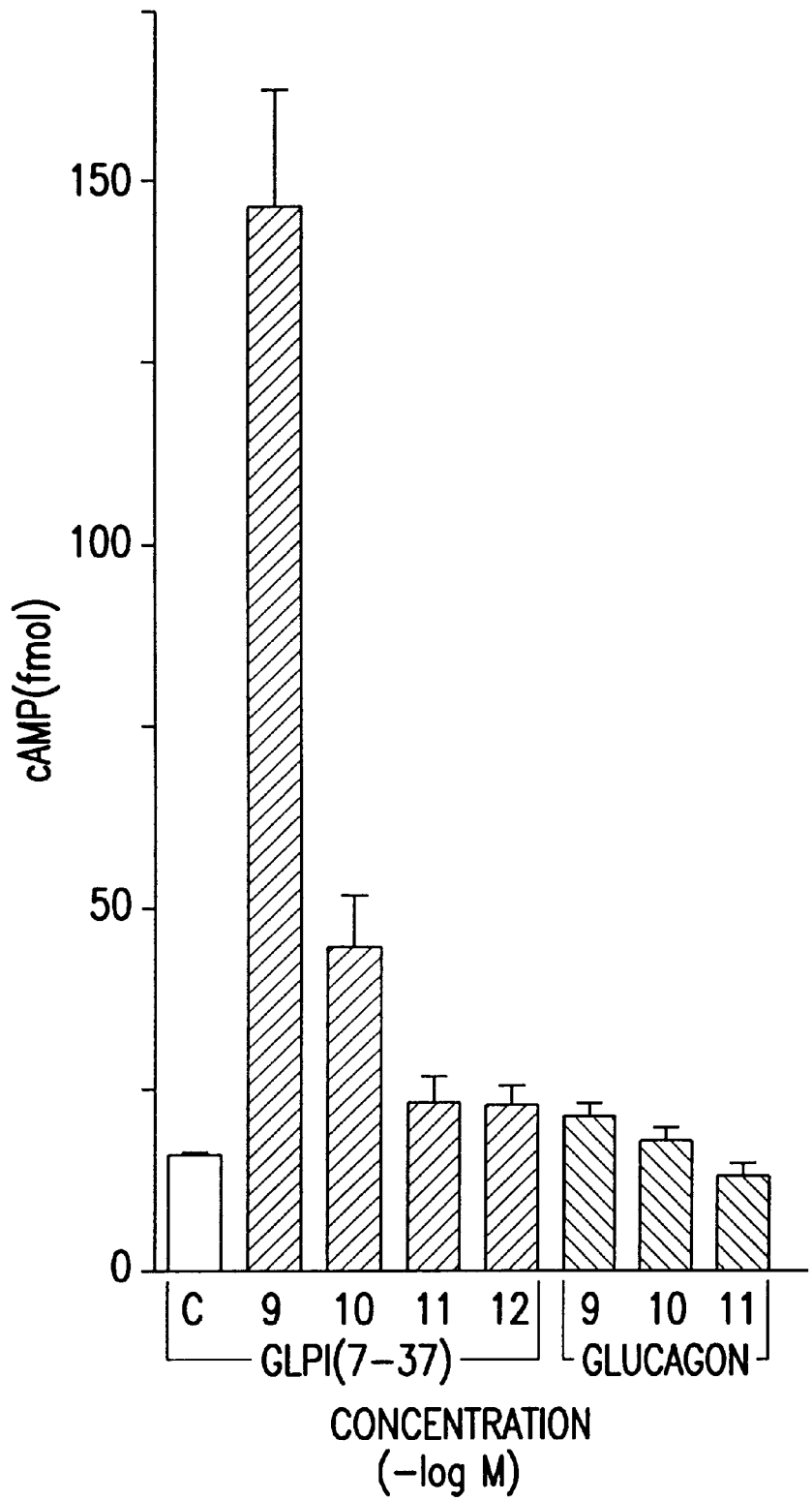
FIG. 2 shows the ability of the insulinotropic peptides glucagon and GLP-1(7-37) to stimulate cAMP formation in the insulinoma line, RIN 1046–38.

The hormone glucagon is known to be synthesized as a high molecular weight precursor molecule which is subsequently proteolytically cleaved into three peptides: glucagon, glucagon-like peptide 1 (GLP-1), and glucagon-like peptide 2 (GLP-2). GLP-1 has 37 amino acids in its unprocessed form. The present invention discloses that the unprocessed GLP-1 is essentially unable to mediate the induction of insulin biosynthesis. The unprocessed GLP-1 peptide is, however, naturally converted to a 31-amino acid long peptide (7-37 peptide) having amino acids 7-37 of GLP-1("GLP-1(7-37)"). Applicant has further discovered that GLP-1(7-37) can undergo additional processing by proteolytic removal of the C-terminal glycine to produce GLP-1(7-36) which also exists predominantly with the C-terminal residue, arginine, in amidated form as arginineamide, GLP-1(7-36) amide. This processing occurs in the the intestine and to a much lesser extent in the pancreas, and results in a polypeptide with the insulinotropic activity of GLP-1(7-37).

A compound is said to have an "insulinotropic activity" if it is able to stimulate, or cause the stimulation of, the synthesis or expression of the hormone insulin. The hormonal activity of GLP-1(7-37) and GLP-1(7-36) appears to be specific for the pancreatic beta (herein "B") cells where it appears to induce the biosynthesis of insulin. The insulinotropic hormone of the invention is useful in the study of the pathogenesis of maturity onset diabetes mellitus, a condition characterized by hyperglycemia in which the dynamics of insulin secretion are abnormal. Moreover, the insulinotropic hormone is useful in the therapy and treatment of this disease, and in the therapy and treatment of hyperglycemia.

Peptide moieties (fragments) chosen from the determined amino acid sequence of human GLP-1 constitute the starting point in the development comprising the present invention. The interchangeable terms "peptide fragment" and "peptide moiety" are meant to include both synthetic and naturally occurring amino acid sequences derivable from a naturally occurring amino acid sequence.

The amino acid sequence for GLP-1 has been reported by several researchers (Lopez, L. C., et al., *Proc. Natl. Acad. Sci., USA* 80:5485–5489 (1983); Bell, G. I., et al., *Nature* 302:716–718 (1983); Heinrich, G., et al., *Endocrinol.* 115:2176–2181 (1984)). The structure of the preproglucagon mRNA and its corresponding amino acid sequence is shown in FIG. 1. This figure further displays the proteolytic processing of the precursor gene product, proglucagon, into glucagon and the two glucagon-like peptides. As used herein, the notation of GLP-1(1-37) refers to a GLP-1 polypeptide having all amino acids from 1 (N-terminus) through 37 (C-terminus). Similarly, GLP-1(7-37) refers to a GLP-1 polypeptide having all amino acids from 7 (N-terminus) through 37 (C-terminus). Similarly, GLP-1(7-36) refers to a GLP-1 polypeptide having all amino acids from number 7 (N-terminus) through number 36 (C-terminus).

In one embodiment, GLP-1(7-36) and its peptide fragments are synthesized by conventional means, such as by the well-known solid-phase peptide synthesis described by Merrifield, J. M. (*Chem. Soc.* 85:2149 (1962)), and Stewart and Young (*Solid Phase Peptide Synthesis* (Freeman, San Francisco, 1969), pages 27–66), which are incorporated by reference herein. However, it is also possible to obtain fragments of the proglucagon polypeptide, or of GLP-1, by fragmenting the naturally occurring amino acid sequence, using, for example, a proteolytic enzyme. Further, it is possible to obtain the desired fragments of the proglucagon peptide or of GLP-1 through the use of recombinant DNA technology, as disclosed by Maniatis, T., et al., *Molecular Biology: A Laboratory Mantual*, Cold Spring Harbor, N.Y. (1982), which is hereby incorporated by reference.

The present invention includes peptides which are derivable from GLP-1(1-37), such as GLP-1(7-36). A peptide is said to be "derivable from a naturally occurring amino acid sequence" if it can be obtained by fragmenting a naturally occurring sequence, or if it can be synthesized based upon a knowledge of the sequence of the naturally occurring amino acid sequence or of the genetic material (DNA or RNA) which encodes this sequence.

Included within the scope of the present invention are those molecules which are said to be "derivatives" of GLP-1(1-37), and especially GLP-1(7-36). Such a "derivative" has the following characteristics: (1) it shares substantial homology with GLP-1(1-37) or a similarly sized fragment of GLP-1(1-37); (2) it is capable of functioning as an insulinotropic hormone and (3) using at least one of the assays provided herein, the derivative has either (i) an insulinotropic activity which exceeds the insulinotropic activity of either GLP-1(1-37) or GLP-1(1-36), or, more preferably, (ii) an insulinotropic activity which can be detected even when the derivative is present at a concentration of $10^{-10}$M, or, most preferably, (iii) an insulinotropic activity which can be detected even when the derivative is present at a concentration of $10^{-11}$ M.

A derivative of GLP-1(1-37) is said to share "substantial homology" with GLP-1(1-37) if the amino acid sequences of the derivative is at least 80%, and more preferably at least 90%, and most preferably at least 95%, the same as that of either GLP-1(1-37) or a fragment of GLP-1(1-37) having the same number of amino acid residues as the derivative.

The derivatives of the present invention include GLP-1 (1-37) fragments which, in addition to containing a sequence that is substantially homologous to that of a naturally occurring GLP-1(1-37) peptide may contain one or more additional amino acids at their amino and/or their carboxy termini. Thus, the invention pertains to polypeptide fragments of GLP-1(1-37) that may contain one or more amino acids that may not be present in a naturally occurring GLP-1(1-37) sequence provided that such polypeptides have an insulinotropic activity which exceeds that of GLP-1(1-37) or GLP-1(1-36).

Similarly, the invention includes GLP-1(1-37) fragments which, although containing a sequence that is substantially homologous to that of a naturally occurring GLP-1(1-37) peptide may lack one or more additional amino acids at their amino and/or their carboxy termini that are naturally found on a GLP-1(1-37) peptide. Thus, the invention pertains to polypeptide fragments of GLP-1(1-37) that may lack one or more amino acids that are normally present in a naturally occurring GLP-1(1-37) sequence provided that such polypeptides have an insulinotropic activity which exceeds that of GLP-1(1-37) or GLP-1(1-36).

The invention also encompasses the obvious or trivial variants of the above-described fragments which have inconsequential amino acid substitutions (and thus have amino acid sequences which differ from that of the natural sequence) provided that such variants have an S insulinotropic activity which is substantially identical to that of the above-described GLP-1derivatives. Examples of obvious or trivial substitutions include the substitution of one basic residue for another (i.e. Arg for Lys), the substitution of one hydrophobic residue for another (i.e. Leu for Ile), or the substitution of one aromatic residue for another (i.e. Phe for Tyr), etc.

Examples of derivatives of GLP-1(1-37) that are useful in the methods of the invention include GLP-1(7-37); GLP-1(7-36); GLP-1(7-35); GLP-1(7-34); and the des-Gly$^{37}$ amidated forms of these molecules. Included as well are the use of additional amino acid residues added to such sequences in order to enhance coupling to carrier protein or amino acid residues added to enhance the insulinotropic effect.

As is known in the art, the amino acid residues may be in their protected or unprotected form, using appropriate amino or carboxyl protecting groups. Useful cations are alkali or alkaline earth metallic cations (i.e., Na, K, Li, ½Ca, ½Ba, etc.) or amine cations (i.e., tetraalkylammonium, trialkylammonium, where alkyl can be $C_1$–$C_{12}$).

The variable length peptides may be in the form of the free amines (on the N-terminus), or acid-addition salts thereof. Common acid addition salts are hydrohalic acid salts, i.e., HBr, HI, or, more preferably, HCl.

B. Assays of Insulinotropic Activity

The present invention concerns GLP-1(1-37) derivatives which have an insulinotropic activity that exceeds the insulinotropic activity of either GLP-1(1-37) or GLP-1(1-36). The insulinotropic property of a compound may be determined by providing that compound to animal cells, or injecting that compound into animals and monitoring the release of immunoreactive insulin (IRI) into the media or circulatory system of the animal, respectively. The presence of IRI is detected through the use of a radioimmunoassay which can specifically detect insulin. Although any radioimmunoassay capable of detecting the presence of IRI may be employed, it is preferable to use a modification of the assay method of Albano, J. D. M., et al., (*Acta Endocrinol.* 70:487–509 (1972)). In this modification, a phosphate/albumin buffer with a pH of 7.4 was employed. The incubation was prepared with the consecutive condition of 500 μl of phosphate buffer, 50 μl of perfusate sample or rat insulin standard in perfusate, 100 μl of anti-insulin antiserum (Wellcome Laboratories; 1:40,000 dilution), and 100 μl of [$^{125}$I] insulin, giving a total volume of 750 μl in a 10×75-mm disposable glass tube. After incubation for 2–3 days at 4° C., free insulin was separated from antibody-bound insulin by charcoal separation. The assay sensitivity was 1–2 μU/ml. In order to measure the release of IRI into the cell culture medium of cells grown in tissue culture, one preferably incorporates radioactive label into proinsulin. Although any radioactive label capable of labeling a polypeptide can be used, it is preferable to use $^3$H leucine in order to obtain labeling of proinsulin. Labeling can be done for any period of time sufficient to permit the formation of a detectably labeled pool of proinsulin molecules; however, it is preferable to incubate cells in the presence of radioactive label for a 60-minute time period. Although any cell line capable of expressing insulin can be used for determining whether a compound has an insulinotropic effect, it is preferable to use rat insulinoma cells, and especially RIN-38 rat insulinoma cells. Such cells can be grown in any suitable medium; however, it is preferable to use DME medium containing 0.1% BSA and 25 mM glucose.

The insulinotropic property of a compound may also be determined by pancreatic infusion. The in situ isolated perfused rat pancreas preparation was a modification of the method of Penhos, J. C., et al. (*Diabetes* 18:733–738 (1969)). In accordance with such a method, fasted rats (preferably male Charles River strain albino rats), weighing 350–600 g, are anesthetized with an intraperitoneal injection of Amytal Sodium (Eli Lilly and Co., 160 ng/kg). Renal, adrenal, gastric, and lower colonic blood vessels are ligated. The entire intestine is resected except for about four cm of duodenum and the descending colon and rectum. Therefore, only a small part of the intestine is perfused, thus minimizing possible interference by enteric substances with glucagon-like immunoreactivity. The perfusate is preferably a modified Krebs-Ringer bicarbonate buffer with 4% dextran T70 and 0.2% bovine serum albumin (fraction V), and is preferably bubbled with 95% $O_2$ and 5% $CO_2$. A nonpulsatile flow, four-channel roller-bearing pump (Buchler polystatic, Buchler Instruments Division, Nuclear-Chicago Corp.) is preferably used, and a switch from one perfusate source to another is preferably accomplished by switching a three-way stopcock. The manner in which perfusion is performed, modified, and analyzed preferably follows the methods of Weir, G. C., et al., (*J. Clin. Investigat.* 54:1403–1412 (1974)), which is hereby incorporated by reference.

C. Formulations of Insulinotropic Compounds

The insulinotropic peptides (or peptide derivatives) of GLP-1(1-37) and especially GLP-1(7-36), may be used as therapeutic compositions. Such therapeutic compositions may consist solely of the insulinotropic peptides (or peptide derivatives) although, preferably, the compositions will contain the insulinotropic peptides (or derivatives thereof) combined in admixture with a pharmaceutically acceptable carrier vehicle.

Suitable vehicles and their formulation, inclusive of other human proteins, e.g., human serum albumin, are described for example in *Remington's Pharmaceutical Sciences* (16th Ed., A. Oslo Ed. Mack, Easton, Pa. (1980)). In order to form a pharmaceutically acceptable composition that is suitable for effective administration to a patient in need of such composition, such compositions will contain an effective amount of GLP-1(7-37), or a derivative of GLP-1(7-37) such as GLP-1(7-36), together with a suitable amount of carrier vehicle.

The GLP-1derivatives of such compounds will preferably have been purified so as to be substantially free of natural contaminants. A material is said to be "substantially free of natural contaminants" if it has been substantially purified from materials with which it is normally and naturally found. Examples of natural contaminants with which GLP-1(7-36) might be associated are: other peptides, carbohydrates, glycosylated peptides, lipids, membranes, etc. A material is also said to be substantially free of natural contaminants if these contaminants are substantially absent from a sample of the material.

Compositions containing GLP-1(7-37) or its derivatives such as GLP-1(7-36) may be administered intravenously, intramuscularly, or sub-cutaneously at dosages in the range of from about 1 pg/kg to 1,000 μg/kg body weight, or at concentrations sufficient to produce serum levels of $10^-$M to $10^{-11}$ M, although a lower or higher dosage may be administered. The required dosage will depend upon the severity of the condition of the patient, for example, the severity of the patient's hyperglycemia, and upon such criteria as the patient's height, weight, sex, age, and medical history. The dose will also depend upon whether the compound of the invention is being administered in a veterinary setting to an animal or to a human patient.

For the purpose of parenteral administration, compositions containing the derivatives of GLP-1(1-37) such as GLP-1(7-36) are preferably dissolved in distilled water and the pH-value is preferably adjusted to about 6 to 8. In order to facilitate the lyophilization process resulting in a suitable product, lactose may be added to the solution. Preferably, the solution is then filtered sterilized, introduced into vials, and lyophilized. In a preferred embodiment, the compound of the invention is administered orally to a patient, at the time of eating or shortly thereafter. The concentration of the GLP-1(1-37) derivatives in these compositions, and especially the concentration of GLP-1(7-36) whether oral or parenteral, may vary from $10^{-12}$M to $10^{-5}$M.

Additional pharmaceutical methods may be employed to control the duration of action. Controlled release preparations may be achieved by the use of polymers to complex or adsorb the GLP-1(1-37) derivatives and especially GLP-1(7-36). The controlled delivery may be exercised by selecting appropriate macromolecules (for example, polyesters, polyamino acids, polyvinyl pyrrolidone, ethylenevinylacetate, methylcellulose, carboxymethylcellulose, and protamine sulfate) and the concentration of macromolecules as well as the methods of incorporation in order to control release. Another possible method to control the duration of action by controlled release preparations is to incorporate the derivatives of GLP-1(1-37), and especially GLP-1(7-36), into particles of a polymeric material such as polyesters, polyamino acids, hydrogels, poly (lactic acid) or ethylene vinylacetate copolymers. Alternatively, instead of incor-porating the GLP-1(1-37) derivatives, and especially GLP-1(7-36), into these polymeric particles, it is possible to entrap these derivatives in microcapsules prepared, for example, by coacervation techniques or by interfacial polymerization, for example, bydroxymethylcellulose or gelatin-microcapsules and poly (methylmethacrylate) microcapsules, respectively, or in colloidal drug delivery systems, for example, liposomes, albumin microspberes, microemulsions, nanoparticles, and nanocapsules or in macroemulsions. Such teachings are disclosed in *Remington's Pharmaceutical Sciences* (1980).

It is possible to enhance the biological half-life of the GLP-1(1-37) derivatives of the present invention, and especially GLP-1(7-36), and, thus, to increase the retention or stability of the derivatives in a recipient, by bonding such derivatives to one or more chemical "moieties" to thereby produce a compound which can be recognized and processed within a recipient to yield a GLP-1(1-37) derivative, and especially GLP-1(7-36). The "moieties" of such compounds may include one or more lipids, carbohydrates, amino acid residues, etc. A preferred "moiety" is an amino acid residue. The most preferred "moiety" is a peptide. The amino terminal residue of GLP-1(7-36) is a preferred site for the bonding of the "moiety."

An appreciation of this aspect of the present invention can be obtained through a consideration of the natural processing of GLP-1(1-37). GLP-1(1-37) has a biological half-life of 15–20 minutes. A natural cleavage of the amino terminal hexapeptide, GLP-1(1-6), occurs to yield GLP-1(7-37) whose biological half-life is only 3–5 minutes. Thus, the amino terminal hexapeptide, GLP-1(1-6) is a natural "moiety" which when bonded to GLP-1(7-37) increases the biological half-life of GLP-1(7-37). The discovery of such a natural "moiety" is disclosed in FIG. 5, and supports the concept that additional or alternative moieties may be employed in the same manner as GLP-1(1-6) to increase the biological half-life of the GLP-1(1-37) derivatives of the present invention, and especially GLP-1(7-36). Although the present invention does not encompass the use of GLP-1(1-6) as a "moiety," it does include variants of GLP-1(1-6) as well as other peptides of unrelated sequence which are capable of enhancing the half-life of the peptides and peptide derivatives of the present invention.

In summary, insulin secretion from the B cell of the endocrine pancreas is controlled by a complex network of metabolic factors. This network includes such diverse components as glucose, amino acids, catecholamines, and peptides. The decoding of the glucagon gene has uncovered two additional glucagon-like peptides encoded in proglucagon, the polypeptide precursor of glucagon. One of these peptides, glucagon-like peptide-1 (GLP-1) is processed from proglucagon in several forms: 37-amino acids GLP-1(1-37), 31-amino acids GLP-1(7-37), and 30 amino acids GLP-1 (7-36). The specific liberation of GLP-1peptides in the intestine and, to some degree, in the pancreas, suggested to the inventors that the GLP-1peptides might be components of the entero-insular axis. To resolve this issue, the effects of the GLP-1peptides on a pancreatic B cell line was studied using a rat perfused pancreas and a cultured rat insulinoma cell-line. These studies have revealed that, in the isolated perfused pancreas, GLP-1(7-37) is a potent stimulator of insulin secretion at concentrations as low as $5\times10^{-12}$M. At $10^{-11}$M, GLP-1(7-36) possesses an insulinotropic activity equivalent to GLP-1(7-37) in the perfused pancreas. Insulin release in response to GLP-1(7-37) is highly dependent upon ambient glucose concentration. The longer peptide (GLP-1 (1-37)) has no insulin-releasing activity even at concentrations as high as $5\times10^{-7}$M. Comparison of the insulinotropic effects of GLP-1(7-37) and glucagon showed that (in the rat perfused pancreas) GLP-1(7-37) is at least 100 fold more potent in the stimulation of insulin secretion. In the rat insulinoma cell line (RIN 1046-38), GLP-1(7-37), at concentrations of $10^{-10}$M to $10^{-11}$M, increased both the cellular levels of cAMP (5-fold) and the levels of insulin mRNA (3-fold) and also stimulated insulin release. Again the effects of GLP-1(7-37) were more potent than those of glucagon. The magnitude of the insulinotropic effects at such low concentrations renders GLP-1(7-37) one of the most potent insulin secretagogues described, including glucagon and gastric inhibitory polypeptide. These results suggest that GLP-1(7-37) and its derivative GLP-1(7-36) may participate in the physiological regulation of pancreatic B cell functions.

Having now fully described the invention, the same will be more readily understood by reference to specific examples which are provided by way of illustration, and are not intended to be limiting of the invention, unless specified.

SPECIFIC EXAMPLES

Example 1

Specificity of GLP-1Peptides

In order to demonstrate that the effects of GLP-1(1-37), GLP-1(1-36) and GLP-1(7-37) were specific for insulin, and were not capable of inducing or provoking non-specific gene expression, the effect of these peptides on the levels of insulin, actin and angiotensinogen mRNAs in rat insulinoma cells were conducted.

Rat insulinoma cells of cell line RIN-38 were derived from a continuous islet cell line, RIN-r, which was established from a transplantable rat islet cell tumor (Gazdar, A. F., et al., *Proc. Natl. Acad. Sci., USA* 77:3519–3523 (1980)).

The cells were maintained in DMEM (Gibco) at a glucose concentration of 4,500 mg/L and supplemented with 10% heat-inactivated fetal bovine serum (Gibco), 100 U/ml of penicillin and 100 µgml of streptomycin. Incubations were carried out at 37° C. in 95% air:5% $CO_2$. Cells grown in the above manner were washed and resuspended in DMEM (Gibco) containing 0.1% bovine serum albumin and 25 mM glucose. Cells were incubated with varying concentrations of insulinotropic peptides (i.e. glucagon, GLP-1(1-37), GLP-1(7-37), or GLP-1(1-36 des-gly-arg amide); Peninsula Laboratories) for six hours, following which the effects of these agents on mRNA expression were determined. In all cases, the concentration of peptides was $10^{-7}M$. Incubations were for six hours.

Messenger RNAs specific for insulin, actin, or angiotensinogen were identified by Northern hybridization as follows: cellular RNA was extracted from solid tumors and cells by homogenization in guanidine thiocyanate and sedimentation through a cesium chloride cushion. Poly $A^+$ RNA was isolated by oligo dT cellulose chromatography (Aviv, H., et al., *Proc. Natl. Acad. Sci., USA* 69:1408–1412 (1972)). Twenty micrograms of total RNA from each sample were fractionated by size on a 1.4% agarose gel after denaturation in glyoxal, followed by electrotransfer to a nylon membrane (Nytran; Schleicher and Schuell). Blotted membranes were baked for two hours at 80° C. under vacuum, prehybridized in 1M NaCl/1% SDS/10% Dextran sulfate at 50° C. overnight and hybridized at the same temperature for 24 h after addition of the labeled probes ($3-5 \times 10^5$ cpm/ml); they were then washed at 55° C. twice in 1×SCC (0.15M NaCl/0.015M Na citrate)/1% SDS), and exposed to X-ray film for varying times at −70° C. with an intensifying screen. The relative amounts of the specific mRNA were determined by microdensitometry. The results of this experiment are shown in Table 1.

The glucagon-like peptides increased the levels of insulin mRNA during 24-hr incubations (Table 1). The increase in insulin mRNA levels was consistently greater in response to the shorter, 31-amino acid peptide; 3-fold higher than control values at 24 hr. These stimulatory effects on insulin mRNA levels and on the release of insulin were observed in the presence of physiologically high (hyperglycemic) (25 mM) and not low (hypoglycemic) (5.5 mM) concentrations of glucose. Evidence that the stimulatory actions of GLP-1are relatively specific for insulin mRNA was obtained by demonstrating that (i) GLP-1(7-37) had negligible effects on levels of actin and angiotensinogen mRNAs in the insulinoma cell line; (ii) glucagon and GLP-2 had no effects on insulin mRNA levels; and (iii) GLP-1(7-37), when added to the rat islet glucagon-producing cell line 1056A and two pituitary cell lines, one producing prolactin (GH4) and the other corticotropin (AtT-20), had no effects on the levels of glucagon, prolactin, and corticotropin mRNAs, respectively.

GLP-1(7-37) was examined to determine whether it could induce the biosynthesis of mRNA of hormones other than insulin. Thus, GLP-1(7-37) (at a concentration of $10^{-7}M$) was added to a rat islet glucagon-producing cell line and two pituitary cell lines (GH4 and AtT-20) which were capable of producing the hormones prolactin and ACTH, respectively, and the amount of hormone specific mRNA produced was determined after 24 hours as described above. GLP-1peptides had no detectable effect on either the level of prolactin mRNA in GH4 pituitary cells, or in the level of ACTH mRNA in AtT-20 pituitary cells.

TABLE 1

Densitometric quantitation of effects of glucagon-like peptides on levels of insulin and actin mRNAs in RIN 1046-38 cells

| | Peptide | Arbitrary densitometric units[1] | | | |
|---|---|---|---|---|---|
| mRNA | conc., M | Control[2] | GLP(1-(1-37) | GLP-1-(7-37) | GLP-1-(1-36)-$NH_2$ |
| | | Experiment 1 | | | |
| Insulin | $5 \times 10^{-7}$ | 1.28 ± 0.18 | 1.87 ± 0.35 | 4.23 ± 0.77[3] | 2.78 ± 0.51[4] |
| Actin | $5 \times 10^{-7}$ | 0.68 ± 0.03 | 0.48 ± 0.06 | 0.72 ± 0.16 | 0.87 ± 0.19 |
| Angiotensinogen | $5 \times 10^{-7}$ | 2.67 ± 0.31 | 2.25 ± 0.20 | 2.78 ± 0.46 | 2.56 ± 0.22 |
| | | Experiment 2 | | | |
| Insulin | $5 \times 10^{-11}$ | 5.90 (6.86, 4.99) | | 7.00 (5.58, 8.41) | |
| | $5 \times 10^{-10}$ | 6.70 (7.92, 5.50) | | | |
| | $5 \times 10^{-9}$ | | | 8.50 (7.59, 9.38) | |
| | $5 \times 10^{-8}$ | | | 7.90 (8.40, 7.40) | |
| Actin | $5 \times 10^{-11}$ | 2.69 (3.23, 2.15) | | 2.11 (1.86, 2.36) | |
| | $5 \times 10^{-10}$ | | | 2.09 (2.38, 1.79) | |
| | $5 \times 10^{-9}$ | | | 2.46 (2.01, 2.92) | |
| | $5 \times 10^{-8}$ | | | 1.99 (2.24, 1.74) | |
| | | Experiment 3 | | | |
| Insulin | $5 \times 10^{-7}$ | 5.56 ± 0.43 | | 1.387 ± 0.40[5] | |
| Actin | $5 \times 10^{-7}$ | 3.29 ± 0.08 | | 4.36 ± 0.44 | |

[1]Determined by scanning of autoradiograms of RNA blots. Values from experiments 1 and 3 are means ± SEM of triplicate plates of cells; values from experiment 2 are means of duplicates (individual values are given in parenthesis). Statistical significance between control and experimental observations were calculated by Student's unpaired two-tailed t test.
[2]No peptide added.
[3]$p < 0.02$.
[4]$p < 0.05$.
[5]$p < 0.001$.

Example 2

The Effect of GLP-1(7-37) on the Transcription of the Insulin and Other Genes The effect of GLP-1(7-37) on the transcription of the insulin and actin genes in RIN-38 insulinoma cells was investigated. Gene transcription rates were determined by quantification of nascent insulin and beta-actin RNA transcripts in nuclei from control and GLP(7-37) treated cells. The GLP-1(7-37) concentration was $10^{-7}$M. Incubation was for 4 hours. Nuclear RNA was hybridized to an excess of cloned specific DNA bound to nitrocellulose and the filters were washed as described by McKnight, G. S., et al., (*J. Biol. Chem.* 254:9050–9058 (1979)). Rat insulin (Ulrich, A., et al., *Science* 196:113–119 (1977)) and, for control, chicken beta-actin cDNAs, provided by Dr. D. Cleveland, the Johns Hopkins University School of Medicine, Baltimore, Md., were used. Hybridization efficiency was controlled through the addition of the hybridization solution of [$^3$H] UTP insulin cRNA. Experiments were done in duplicate and values are expressed in ppm/kb of cDNA insert, corrected for efficiency of hybridization (40–50%). The results of this experiment revealed that GLP-1(7-37) increased the rate of insulin gene transcription, but had no detectable effect upon the rate of actin gene transcription.

Example 3

Effect of GLP-1 Derivatives on Cellular cAMP Levels

In order to determine whether glucagon-like proteins were capable of affecting cellular cAMP levels, the effects of GLP-1(7-37) and GLP-1(1-37) on cAMP levels in RINS-38 insulinoma cells (Expt. I and Expt. II in Table 2, respectively) was determined.

Cells were grown as described in Example 1, in 26 well culture dishes. Varying amounts of glucagon-like peptides were added to culture wells in triplicate. After permitting incubation for 10 minutes, the total cell media was examined for cAMP, and the concentration of cAMP was determined. The results of this experiment are shown in Table 2. Twenty microliters from each culture well was assayed.

TABLE 2

| Peptide Concentration (M) | Expt. I | Expt II |
|---|---|---|
| 0 | 140 | 91 |
| $10^{-6}$ | 400 | 170 |
| $10^{-7}$ | 370 | 120 |
| $10^{-8}$ | 494 | 160 |
| $10^{-9}$ | 515 | 100 |
| $10^{-10}$ | 253 | 90 |
| $10^{-11}$ | 533 | 90 |

This experiment reveals that GLP-1(7-37) was capable of stimulating cAMP levels even when present at a concentration of $10^{-11}$M. The increase in cAMP levels is an indication that GLP-1(7-37) is capable of interacting with cellular receptors. In contrast, neither GLP-1(1-37) nor GLP-2 (GLP-2) exhibited such activity.

A further experiment was performed in order to compare the insulinotropic activities of GLP-1(1-37), GLP-1-(1-36)-NH$_2$ and GLP-1(7-37) with the insulinotropic activity of glucagon. The procedures for this experiment are the same as those described above. The results of this experiment are shown in Table 3.

At the relatively high concentration of 0.5 μM, GLP-1(1-37), GLP-1-(1-36)-NH$_2$, GLP-1(7-37) and glucagon each increased cAMP levels. At 5 nM, GLP-1-(7-37) increased cAMP levels at least 4-fold and was still active at 50 pM. In contrast, the effects of glucagon, GLP-1-(1-37), and GLP-1-(1-36)-NH$_2$ on the formation of cAMP were negligible at these concentrations.

The ability of the insulinotropic peptides glucagon and GLP-1(7-37) to stimulate cAMP formation in the insulinoma line, RIN 1046-38, was investigated. Insulinotropic activity was monitored as described by Mojsov, S., et al., (*J. Clin. Invest.* 79:616–619 (1987)) and Drucker, D. J., et al., (*Proc. Natl. Acad. Sci.* 84:3434–3438 (1987)), both of which references are incorporated by reference herein. The results of this study are shown in FIG. 2, and indicate that GLP-1 (7-37) is at least 1000 times more potent than glucagon in inducing cAMP formation.

TABLE 3

Stimulation of cAMP formulation by glucagon and glucagon-like peptide in RIN 1046-38 cells

| Exp. | Peptide conc., M | No. of plates | Control | cAMP, fmol* (mean ± SEM) | | | |
|---|---|---|---|---|---|---|---|
| | | | | GLP-1 (7-37) | Glucagon | GLP-1(1-37) | GLP-1 (1-36)-NH$_2$ |
| 1 | no peptide | 8 | 15.4 ± 0.7* | | | | |
| | 5 × $10^{-12}$ | 5 | | 21.0 ± 2.0 (a) | 18.7 ± 2.2 (NS) | | |
| | 5 × $10^{-11}$ | 5 | | 23.9 ± 1.0 (c) | 13.2 ± 1.0 (NS) | | |
| | 5 × $10^{-10}$ | 5 | | 45.2 ± 5.9 (c) | 16.5 ± 2.0 (NS) | | |
| | 5 × $10^{-9}$ | 5 | | 148.0 ± 15.0 (c) | 20.1 ± 2.5 (a) | | |
| 2 | No peptide | 4 | 43.6 ± 4.1 | | | | |
| | 5 × $10^{-8}$ | 4 | | 78.3 ± 3.1 (c) | 44.8 ± 1.6 (NS) | | |
| | 5 × $10^{-7}$ | 4 | | 83.0 ± 2.1 (c) | 93.1 ± 2.9 (c) | | |
| 3 | No peptide | 5 | 34.4 ± 5.2 | | | | |
| | 5 × $10^{-10}$ | 5 | | 70.8 ± 5.2 (a) | | 27.6 ± 4.6 (NS) | |
| | 5 × $10^{-9}$ | 5 | | 134.0 ± 25.6 (b) | | 24.3 ± 1.9 (NS) | |
| | 5 × $10^{-8}$ | 5 | | 69.6 ± 7.0 (b) | | 30.8 ± 2.8 (NS) | |
| | 5 × $10^{-7}$ | 5 | | | | 69.9 ± 2.6 (c) | |
| 4 | 5 × $10^{-7}$ | 4 | 41.3 ± 7.1 | | | | 70.2 ± 2.8 (b) |

Statistical significance between control (no peptide) and experimental observations (by unpaired two-tailed t test) is as follows: a ($P < 0.05$); b ($P < 0.01$); c ($P < 0.001$); NS, not significant.
*All values are per 1/50th of cell extract per plate.

Example 4

Effect of GLP-1Peptides on Insulin Production

Rat insulinoma cells of cell line RIN-38 were grown in DME medium as described in Example 1. After incubation with $5\times10^{-7}$M GLP-1(7-37), the concentrations of insulin in the cell culture mediums were determined by radioimmunoassay (as described above). Insulin protein levels were determined after incubation for 1 or 24 hours. The results of this experiment are shown in Table 4.

TABLE 4

| Peptide Added | Insulin Produced ($\mu$ units/ml) | |
| --- | --- | --- |
|  | 1 Hour | 24 Hours |
| None | 166 | 2,778 |
| GLP-7 (7-37) | 381 | 5,164 |

Example 5

Pancreatic Perfusion Assay of Insulinotropic Activity

The pancreas of a live rat was perfused with varying concentrations of GLP-1(1-37) and GLP-1(7-37) as described above. Isolated rat pancreas was prepared according to the method of Weir, G. C., et al., (*J. Clin. Invest.* 54:1403–1412 (1974)), and Penkos, J. C., et al. (*Diabetes* 18:733–738 (1969)). The perfusate contained bicarbonate buffer (pH 7.4) and 120 mg/dl glucose, 4% dextran T-70, and 0.2% bovine serum albumin, and was equilibrated with 95% oxygen and 5% carbon dioxide. The first 20 minutes of each perfusion was an equilibrium period. After this initial period, aliquots of perfusate were removed every 2–4 min for additional 20 min, thus allowing the system to equilibrate for a total of 40 min. The perfusion, including any added insulinotropic peptide, was for 6 min and samples were collected at 1-min intervals. When more than one perfusion was to be performed, the peptide perfusions were followed by equilibration periods of 20 min, during which four samples 5 min apart were collected. A second 6-min perfusion followed with the same peptide as the first perfusion only at 100 times higher concentration of peptide. Again, samples 1 min apart were collected. The entire perfusion time was between 70 and 85 min.

In each aliquot of perfusate obtained, insulin was determined by radioimmunoassay. In addition, the efficiency of delivery of the insulinotropic peptide was confirmed by radioimmunoassay of corresponding aliquots of perfusate in which insulin was measured (Mojsov, S. G., et al., *J. Biol. Chem.* 261:11880–11889 (1986), which reference is incorporated herein by reference). At one minute intervals, pancreas effluent insulin levels in picograms/ml were determined by radioimmunoassay (as described above). The results of this experiment are shown in Table 5. Perfusions were done using peptide concentrations of $5\times10^{-7}$M, $5\times10^{-8}$M, and $5\times10^{-10}$M, $5\times10^{-11}$M, and $5\times^{-12}$M. Peptides were add after the zero minute effluent value had been determined.

GLP-1(1-37) was found to mediate a 3.4-fold increase in effluent insulin concentrations when perfused into rat pancreas at a concentration of $5\times10^{-7}$M; at a concentration of $5\times10^{-8}$M, this peptide was capable of mediating only a two-fold increase in serum insulin levels. At a concentration of $5\times10^{-10}$M, this peptide was found to mediate only a 20% increase in serum insulin levels. The observed insulinotropic activity of GLP-1(1-37) in these experiments most probably reflects the presence of GLP-1(7-37) in the preparations (either through the degradation of GLP-1(1-37) or due to low level contamination).

GLP-1(7-37) was found to be capable of stimulating a 132-fold increase in insulin levels when provided to rat pancreas at a concentration of $5\times10^{-7}$M. At a 10-fold lower concentration ($5\times10^{-8}$), this peptide was capable of directing a 21-fold increase in the effluent concentration of insulin. At a concentration of $5\times10^{-10}$M, GLP-1(7-37) was found to be capable of mediating an increase in effluent insulin levels (32-fold). Even at a concentration of $5\times10^{-11}$M, GLP-1(7-37) delivered a 15-fold increase in insulin levels whereas GLP-1(1-37) was without effect. $10^{-12}$M gave an insulinotropic effect in studies described in Weir et al. (*Diabetes* 38:338–342 (1989)).

This experiment shows that GLP-1(7-37) is more than 1,000-fold more potent than GLP-1(1-37) in stimulating insulin expression in vivo. In addition, the GLP-1peptides had no effects on the release of the peptide hormone glucagon in these same experiments. Thus, the stimulatory effects of GLP-1are specific for the beta (B) cells and do not act on pancreatic alpha (A) or delta (D) cells.

The level of GLP-1(1-37) and GLP-1(7-37) in rat portal blood has been measured by radioimmunoassay to be approximately 150 pg/ml (50 pM). The corresponding level in peripheral blood is 50 pg/ml (15 pM). The above-described results were obtained using GLP-1(7-37) at a concentration of 5–50 pM. Thus, these results indicate that GLP-1(7-37) has insulinotropic activity at its physiologic concentration.

TABLE 5

| | | Insulin Produced (picograms/ml) at Peptide Concentration | | | | |
| --- | --- | --- | --- | --- | --- | --- |
| | Minutes | $5\times 10^{-7}$M | $5\times 10^{-8}$M | $5\times 10^{-10}$M | $5\times 10^{-11}$M | $5\times 10^{-12}$M |
| GLP-1 (7-37) | 0 | 50 | 925 | 205 | 160 | 50 |
| | 1 | 6,600 | 20,700 | 7,400 | 2,400 | 50 |
| | 2 | 4,700 | 10,500 | 1,800 | 1,700 | 50 |
| | 3 | 1,700 | 4,000 | 760 | 1,900 | 98 |
| GLP-1 (1-37) | 0 | 1,400 | 3,000 | 500 | 340 | 50 |
| | 1 | 4,700 | 6,000 | 600 | 180 | 50 |
| | 2 | 2,900 | 2,000 | 640 | 230 | 160 |
| | 3 | 2,200 | 2,000 | 430 | 340 | 50 |

Example 6

Comparison of the Insulinotropic Activities of Glucagon and GLP-1(7-37)

Figure 3:
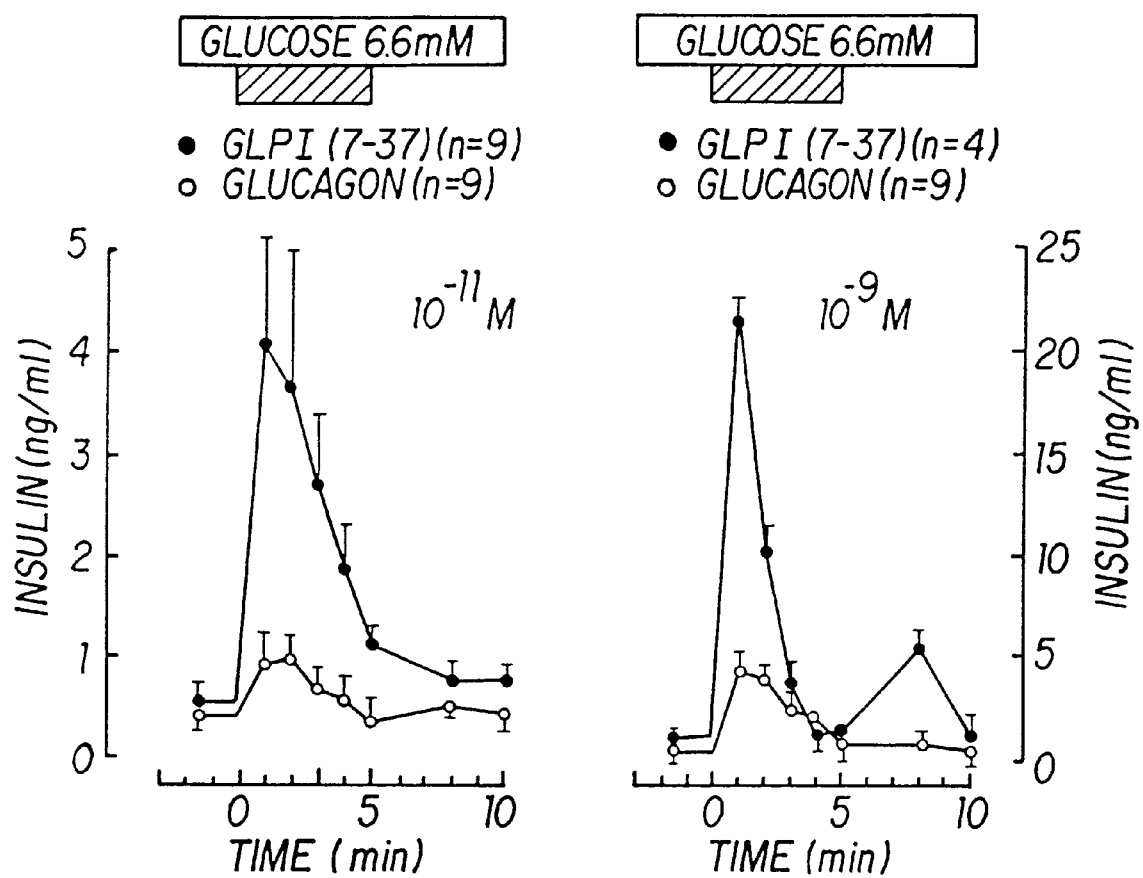
FIG. 3 shows a comparison of the insulinotropic activity of glucagon with that of GLP-1(7-37).

Rat pancreas perfusion experiments were conducted as described in Example 5, in order to compare the insulinotropic activity of glucagon with that of GLP-1(7-37). Peptides were perfused (for 5 minutes) at concentrations of $10^{-9}$M and $10^{-11}$M. As shown in FIG. 3, GLP-1(7-37) was found to have more than 100 times the insulinotropic activity of glucagon.

This finding is confirmed by the study of the effects of glucagon, GLP-1(1-37), and GLP-1(7-37) on the cAMP levels in RIN 1046-38 insulinoma cells which is presented in Table 3.

Example 7

Insulinotropic Activity of Derivatives of GLP-1(1-37)

Figure 4:
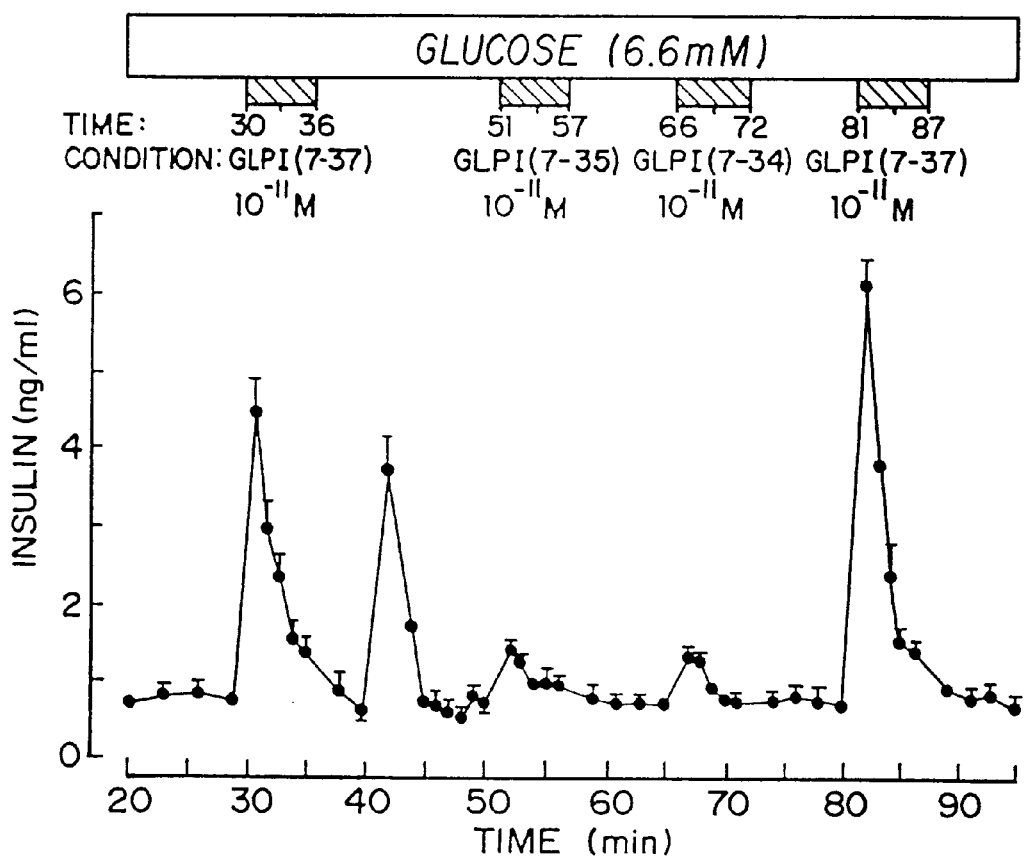
FIG. 4 shows a comparison of the insulinotropic activities of GLP-1(7-34), GLP-1(7-35), and GLP-1(7-37) using the rat pancreas perfusion technique.

The insulinotropic activities of GLP-1(7-34) and GLP-1(7-35) were compared to that of GLP-1(7-37) using the rat pancreas perfusion technique described above. Five minute perfusions were employed. As shown in FIG. 4 all three of these peptides had detectable insulinotropic activity at a concentration of $10^{-11}$ M. These results indicate that the tested derivatives of GLP-1(7-37) all have an insulinotropic activity greater than that of GLP-1(1-37, which is inactive at $10^{-11}$ M).

The GLP-1related peptides: GLP-1(7-36)-NH$_2$ and GLP-1(7-37) were compared to determine their relative insulinotropic activities. Insulinotropic activity was determined using the pancreatic perfusion assay of Example 6; the perfusion being carried out for 5 minutes. Peptides were present at a concentration of $10^{-11}$ M. The results of this experiment are shown in Table 6. These results indicate that both GLP-1(7-37) and GLP-1(7-36)-NH$_2$ have substantial insulinotropic activity.

TABLE 6

Comparison of the Insulinotropic Activity of GLP-1 (7-37) and GLP-1 (7-36)-NH$_2$

| Time (Minutes) | GLP-1 (7-36)-NH$_2$ | GLP-1 (7-37) |
|---|---|---|
| −1 | 985 ± 275 | 1330 ± 280 |
| +1 | 4550 ± 703 | 4200 ± 784 |
| +2 | 3330 ± 637 | 3280 ± 889 |
| +3 | 2500 ± 564 | 2500 ± 505 |

The effects of GLP-1(7-37) and GLP-1(7-36)-NH$_2$ on cAMP formation in the insulinoma cell line RIN 1046-38 was determined using the procedure of Example 1. Cells were incubated for 10 minutes in the presence of 0, $10^{-11}$, $10^{-9}$, or $10^{-7}$ M peptides. The results of this experiment are shown in Table 7. These results confirm that both GLP-1 (7-37) and GLP-1(7-36)-NH$_2$ are insulinotropic peptides.

TABLE 7

EFFECTS OF GLP-1(7-37) VERSUS GLP-1(7-36)NH$_2$ ON cAMP FORMATION IN AN INSULINOMA CELL LINE (RIN 1046-38 CELLS).

| | | IBMX | Peptide Concentration (M) | | |
|---|---|---|---|---|---|
| Peptide | N | (uM) | 0 | $10^{-11}$ | $10^{-9}$ | $10^{-7}$ |
| None (Control) | 8 | 100 | 161 ± 10* | | | |
| GLP-1(7-37) | 4 | 100 | | 205 ± 9 | 202 ± 17 | 317 ± 65 |
| GLP-1(7-36)NH$_2$ | 4 | 100 | | 141 ± 5 | 225 ± 16 | 358 ± 32 |
| None (Control) | 8 | 500 | 540 ± 22 | | | |
| GLP-1(7-37) | 4 | 500 | | 501 ± 49 | 927 ± 75 | 2114 ± 421 |
| GLP-1(736)NH$_2$ | 4 | 500 | | 446 ± 38 | 1199 ± 41 | 1676 ± 113 |

*All cAMP values are given as/fmoles/10 ul of cell extract

Example 8

Stability of GLP-1(1-37)

Figure 5:
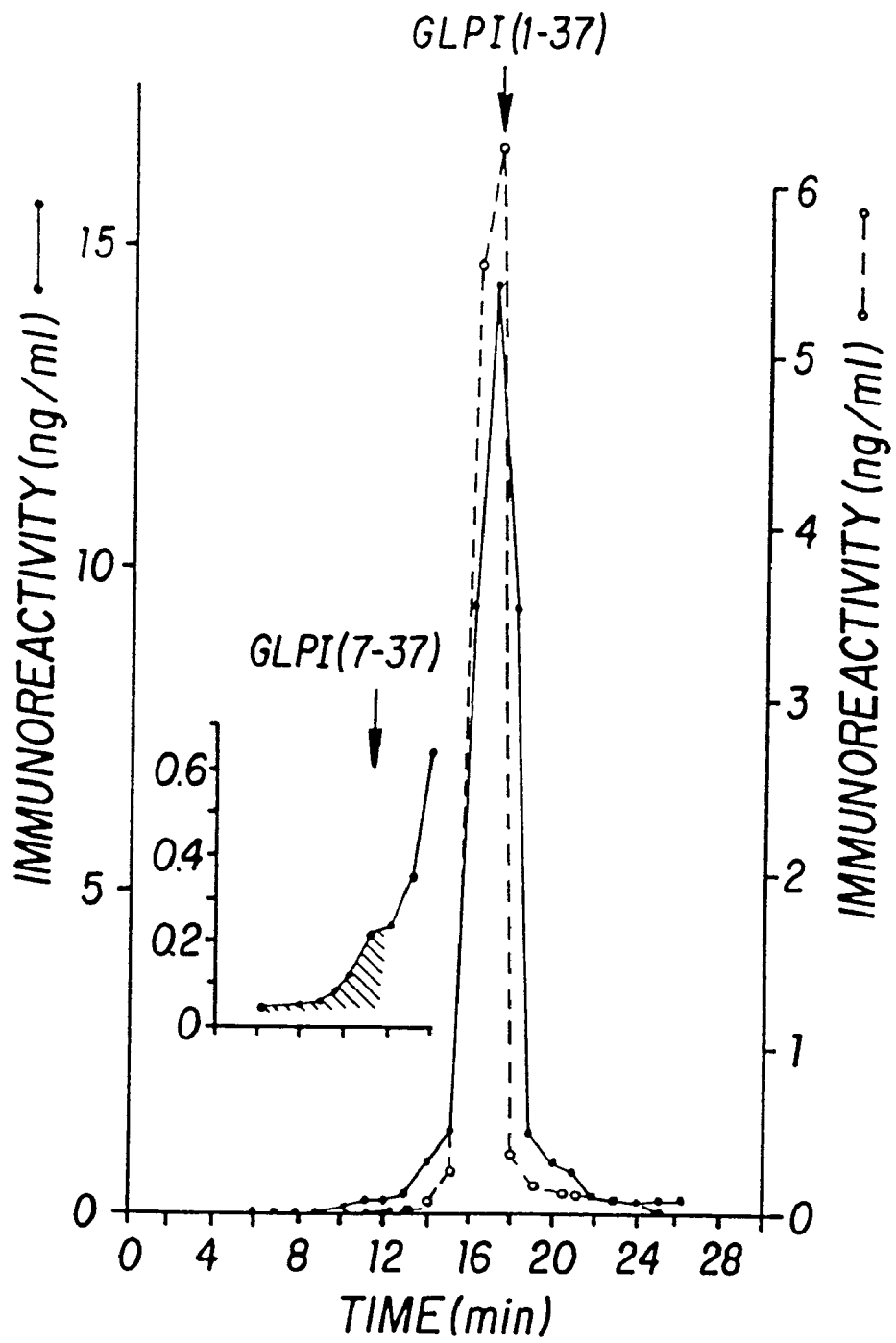
FIG. 5 shows the breakdown of GLP-1(1-37) into GLP-1(7-37) under experimental conditions.

To assess the stability of the 37 amino acid peptide in the experimental conditions, GLP-1(1-37) was incubated for 24 hr in culture medium alone or in medium supplemented with either 0.1% bovine serum albumin or 10% fetal bovine serum. Aliquots of media were analyzed by high-pressure liquid chromatography and radioimmunoassay. Before incubation, no GLP-1(7-37) was detected in the preparation of GLP-1(1-37) (FIG. 5). However, after incubation of GLP-1(1-37) in conditioned medium containing 0.1% bovine serum albumin, a small peak of GLP-1(7-37) appeared, indicating that cleavage of GLP-1(1-37) to the smaller, more active GLP-1(7-37) occurs under these experimental conditions.

Example 9

Insulinotropic Effect of GLP-1(8-37)

As discussed above, glucagon has been found to be a pancreatic betacell (B cell) secretagogue, acting at concentrations as low as $10^{-9}$ M. GLP-1(7-37), which is co-encoded on the preproglucagon gene, has, as shown above, the capacity to mediate an insulinotropic effect even at concentrations as low as $10^{-12}$ M. In order to determine if separate receptors might be involved in the recognition of glucagon and GLP-1(7-37), a potential GLP-1 antagonist, the analog des-7 histidine GLP-1(7-37) was constructed. This analog is hereinafter referred to "GLP-1(8-37)."

Insulin secretion was studied in the perfused rat pancreas assay described above, with a perfusate glucose level of 6.6 mM. GLP-1(8-37) was found to have no detectable effect at concentrations at $10^{-11}$, $10^{-9}$, or $10^{-8}$ M. A weak insulinotropic activity was detected at $10^{-7}$ M. At a perfusate glucose level of 16.7 mM, the analog had no effect at $10^{-9}$ M.

A similar experiment was conducted using glucagon. Glucagon was infused into rat pancreas for 5 minutes at a concentration of $10^{-9}$ M with a perfusate glucose level of 6.6 mM, in either the presence or absence of $10^{-8}$ M GLP-1(8-37). Glucagon was found to elicit an elevated mean perfusate insulin concentration of 4.98±0.96 ng/ml, and virtually identical results (5.26±0.89 ng/ml) were seen with glucagon in the presence of GLP-1(8-37) (N=4).

The above described protocol was used to study the effects of the GLP-1(7-37) in the presence or absence of GLP-1(8-37). GLP-1(7-37), alone at a concentration of $10^{-11}$ M stimulated mean insulin release of 2.25±0.30 ng/ml. This response was, however, lower (1.30±0.19 ng/ml (P<0.025, N=7 for each)) when the same dose was given on a background of the analog. These data indicate that the removal of the 7-histidine from GLP-1(7-37) leads to a loss of agonist function in this system, and that agonist properties are revealed. Because the agonist activity could only be demonstrated against GLP-1(7-37), and not against glucagon, these two secretagogues appear to act through separate receptors.

Using the above-described perfused rat pancreas system, and a glucose perfusate of 6.6 mM, it was found that $10^{-9}$ M GLP-1(7-37) was capable of eliciting a biphasic pattern of insulin secretion with an initial spike of release followed by the plateau of sustained release. Furthermore, this response was found to be glucose-dependent; at $10^{-9}$ M and a perfusate glucose concentration of 2.8 mM, no stimulation of insulin release was seen; at a perfusate glucose concentration of 6.6 mM or 16.7 mM, the mean incremental release above control was 4.7±1.0 or 22.8±4.7 ng/ml, respectively. GLP-1(7-37) was found to be extraordinarily potent. At concentrations of $10^{-12}$ M it was found to stimulate insulin secretion at a perfusate glucose concentration of 6.6 mM from a base line of 0.8±0.2 ng/ml to a peak of 1.6±0.5 ng/ml (P<0.05). When infused at $10^{-11}$ M, insulin release was stimulated to a peak of 4.1±1.4 ng/ml and at $10^{-9}$ M, a peak of 23.1±1.3 ng/ml was obtained. It is not yet known whether this GLP-1peptide is secreted as the 7-37 form or is the 7-36-amide; both compounds were equally potent secretagogues.

Synthetic glucagon was far less potent with no release found at $10^{-11}$ M. At $10^{-9}$ M, however, glucagon was found to produce a peak of 4.5±0.5 ng/ml.

Thus, GLP-1(7-37) and the 7-36-amide are candidates for physiological regulation as an "incretin" or as and endocrine modulator.

Example 10

Effects of GLP-1(8-37) on cAMP Formation in an Insulinomina Cell Line

A comparison of the insulinotropic effects of GLP-1(8-37), GLP-1(7-37) and glucagon on cAMP formation by the insulinoma cell line RIN 1046-38 was determined using the procedure of Example 1. The results of this experiment is shown in Table 8. These results show that GLP-1(8-37) has an insulinotropic activity which is comparable to that of glucagon, and that GLP-1(7-37) has an insulinotropic activity which is more than 100 times greater than that of either GLP-1(8-37) or glucagon.

TABLE 8

Effects of GLP-1 (8-37) versus GLP-1 (7-37) and Glucagon on cAMP Formation in an Insulinoma Cell Line (RIN 1046-38 cells)

| Peptide | Concentration (M) | cAMP Formation* |
|---|---|---|
| None | | 27 ± 2 |
| GLP-1 (8-37) | $10^{-8}$ | 28 ± 0.8** |
| | $10^{-7}$ | 24 ± 2 |
| | $10^{-6}$ | 31 ± 3 |
| | $10^{-5}$ | 77 ± 11 |
| GLP-1 (7-37) | $10^{-8}$ | 128 ± 10 |
| Glucagon | $10^{-6}$ | 92 ± 9 |

*All cAMP levels are given as f-mole/5 ul of cell extract/15 min exposure to peptide
**Means ± S.E.M. (n = 4)

Example 11

The experiments and results presented below pertain to the administration of GLP-1(7-37) to non-insulin dependent (type II) diabetic and non-diabetic subjects. Non-insulin dependent (type II) diabetes (NIDDM) is also known as "maturity-onset diabetes." Two types of experiments were performed. In the first set of experiments, the effect of GLP-1(7-37) infusion on glucose and insulin levels of fasting individuals (diabetic and non-diabetic) was determined. In the second set of experiments, the effect of GLP-1(7-37) infusion on glucose and insulin levels at mealtimes was evaluated.

For all experiments, GLP-1(7-37) was synthesized by the stepwise solid-phase method of Merrifield, R. B. (*J. Am. Chem. Soc.* 95:2149–2154 (1963)). The peptide was purified by preparative reverse-phase C-18 chromatography on a Water Delta-Prep apparatus. The purified peptide was shown to be homogenous by amino acid analysis, preview-sequence analysis, and high performance liquid chromatography (HPLC) on reverse-phase C-18 in two different solvent systems, ion-exchange DEAE-52 columns and mass spectral analysis.

For all experiments, plasma glucose levels were determined with a hexokinase assay, GLP-1(7-37) and insulin (Soeldner et al., *Diabetes* 14:771–777 (1965)) was measured with radioimmunoassays in plasma and serum samples, respectively. Samples for GLP-1(7-37) were collected into EDTA containing tubes with 1,000 IU of aprotonin (trasylol) per ml of blood. The tubes were kept at 4° C. and plasma was separated within 5 minutes of collection. Plasmas and sera were kept frozen at −20° C. until they were assayed. The radioimmunoassay for GLP-1(7-37) was performed in 0.1 M sodium borate buffer, pH 8.2, containing 5% bovine serum albumin, 50 mM EDTA, 0.1 M benzamidine and 0.2% merthiolate. Plasma samples (0.05 ml), antiserum (0.4 ml at a final dilution of 1:10,000) and radioiodinated GLP-1(7-37) (0.6 ml, 8,000–8,500 cpm) in a total volume of 1.2 ml were incubated for four days at 4° C. Separation of antibody-bound from free peptide was accomplished with dextran-coated charcoal. This assay is identical to the assay previously reported by Mojsov et aL. (*J. Biol. Chem.* 261:11880–11889 (1986)) and has a detection limit of 5 pg/ml. It has less than 0.001% cross-reactivity with glucagon, GLP-1, GLP-2, and insulin. The inter- and intra-assay coefficients of variation for the GLP-1(7-37) and insulin assays were less than 10% and 5% respectively. Hemoglobin $A_{1c}$ was measured with an HPLC method with inter- and intra-assay coefficients of variation <2.5% and a non-diabetic range of 3.8–6.4% as described by Nathan, D. M. (*Clin. Chem.* 27:1261–1263 (1981)). Statistical analyses were performed with students paired and unpaired 2-tailed t-test, as indicated, using the Clinfo system.

In order to determine the therapeutic utility of GLP-1(7-37) in the treatment of hyperglycemia and maturity onset diabetes, four healthy non-diabetic and seven type II diabetic males and two type II diabetic females between 18 and 65 years of age and with no known history of other diseases were recruited. The non-diabetic subjects had no history of glucose intolerance or obesity and no family history of diabetes. The only selection criteria for the type II diabetic subjects were that they were in generally good health, had never received insulin therapy and had been treated with diet alone. The baseline characteristics of the subjects are shown in Table 9.

TABLE 9

Characteristics of the Non-diabetic and type II Diabetic Subjects Studied

| Subject | Non-diabetic (n = 4) | Diabetic (n = 9) |
|---|---|---|
| Age (years) | 16.5 ± 3.0 | 54.4 ± 7.8 |
| Ideal body weight (%) | 99.0 ± 1.5 | 128 ± 23.0 |
| Duration diabetes (years) | — | 4.8 ± 5.1 |
| Hemoglobin $A_{1c}$ (%) | 4.88 ± 0.4 | 7.67 ± 1.2 |
| All values expressed as mean ± S.D. | | |

Subjects were requested to fast for at least 10 hours prior to the morning of testing. Intravenous lines were placed in each arm, one for withdrawal of blood specimens and one for the administration of GLP-1(7-37). An infusion of normal saline was used to keep the intravenous line open. After 45 minutes of saline infusion during which blood specimens were obtained every 15 minutes, either GLP-1(7-37) or continued saline was infused (flarard Infusion Pump 22, Harvard Apparatus, Inc., So. Natick, Mass.). GLP-1(7-37) was infused at 1.25, 2.5, 5.0 or 20 ng/kg/min for 30 minutes on separate mornings. Blood samples were obtained every 5 minutes during the 30-minute infusion, at 2-minute intervals for 10 minutes after the cessation of the GLP-1(7-37) infusion to allow determination of the peptide disappearance rates, and at 15- to 30-minute intervals for another 90 to 120 minutes.

Subjects were admitted on separate mornings for the infusion of either GLP-1(7-37) or saline. Neither the subject nor the investigators knew whether placebo or test substance was being administered, and the order of administration was randomized. During the infusions, subjects were asked to perform mental arithmetic in order to test for symptoms of hypoglycemia (low blood sugar). In addition, blood pressures and pulse rates were measured every 15 minutes. Studies were preformed with the subjects continuing to fast during the entire study period (in fasting studies, non-diabetic subjects n=3, diabetic subjects n=5) or with a standard breakfast meal (450 calories, 50% carbohydrate, 30% fat and 20% protein) consumed during the first 15–20 minutes of the GLP infusion ("meal studies" in non-diabetic subjects n=1, diabetic subjects n=5). All meal studies were performed with a 5 ng/kg/min GLP-1(7-37) infusion.

1) Results of Experiments with Fasting Individuals a) Normal Subjects

Figure 6:
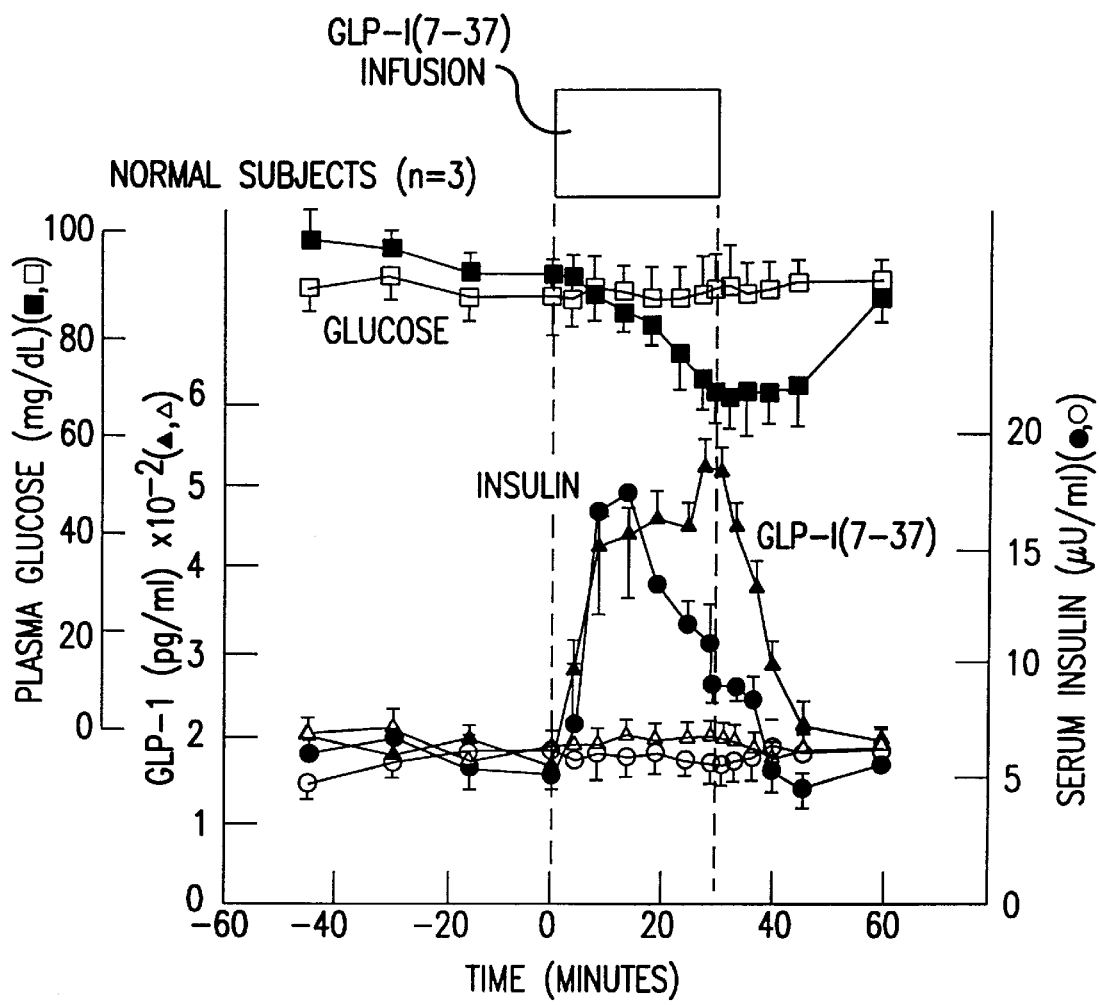
FIG. 6 shows plasma glucose levels and serum insulin levels in fasting normal subjects during infusion of GLP-1 (7-37).

FIG. 6 shows that the infusion of GLP-1(7-37) in normal, non-diabetic fasting human subjects stimulates insulin secretion and lowers plasma glucose levels. GLP-1(7-37) or saline was infused into three subjects at a rate of 5.0 ng/kg/min for 30 minutes after an overnight fast. Levels of insulin and GLP-1(7-37) were measured by radioimmunoassays. Measurements obtained for the GLP-1(7-37) and saline placebo infusions are shown in closed and open symbols, respectively. Values shown are means±SEMs.

The fasted non-diabetic subjects were found to respond to GLP-1(7-37) (5 ng/kg/min) with an approximately 3-fold increase in insulin levels from 6.5±1.6 $\mu$U/ml at time 0 to a mean peak value of 17.7±8.6 $\mu$U/ml at 15 minutes after the beginning of the peptide infusion (FIG. 6). Insulin levels peaked midway during the infusion (at 15 min) and began to decline during the infusion despite stable elevated GLP-1 (7-37) levels, but concurrent with a fall in plasma glucose. Glucose concentrations declined from a mean baseline value of 90±6 mg/dL (5.0±0.33 mmol/L) to a nadir of 68±6 mg/dL (3.78±0.33 mmol/L) 34 minutes after the infusion began. One subject had symptoms consistent with mild hypoglycemia concurrent with a plasma glucose level of 62 mg/dL (3.44 mmol/L). GLP-1(7-37) levels rose by approximately 2.5-fold during the infusion. The insulin levels begin to fall after 15–20 minutes of the GLP-1(7-37) infusion, concomitant with the fall in plasma glucose levels. One explanation is that the fall in insulin levels is a consequence of the direct dependency of the insulinotropic actions of GLP-1(7-37) on the blood glucose levels (Weir et al., *Diabetes* 38:338–342 (1989)).

b. Diabetic Subjects

Figure 7:
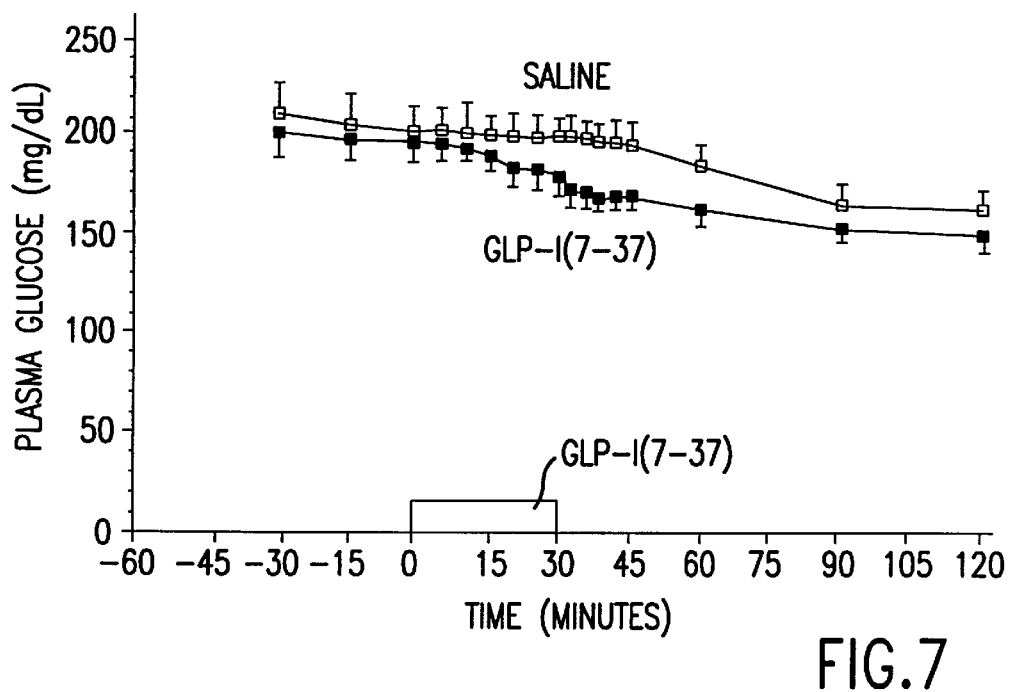
FIGS. 7 and 7A shows plasma glucose levels and serum insulin levels in fasting maturity onset diabetic subjects during infusion of GLP-1(7-37). Values are on the basis of relative percentage changes from the baseline.
Figure 8:
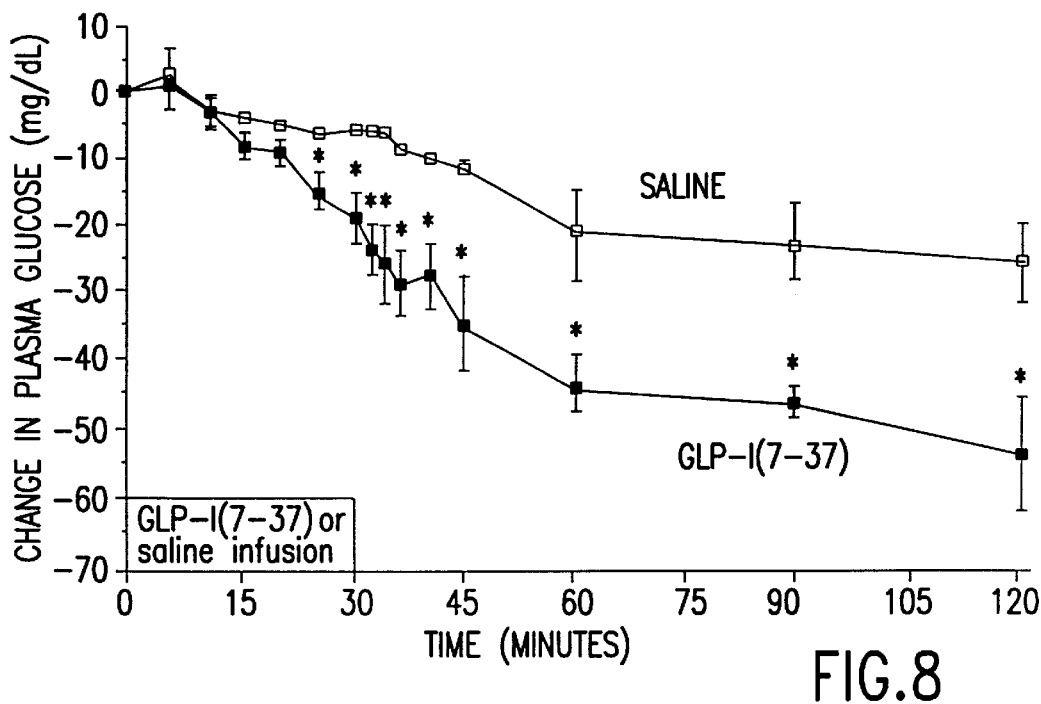
FIGS. 8 and 8A shows absolute plasma glucose levels and serum insulin levels in fasting maturity onset diabetic subjects during infusion of GLP-1(7-37).
Figure 8A:
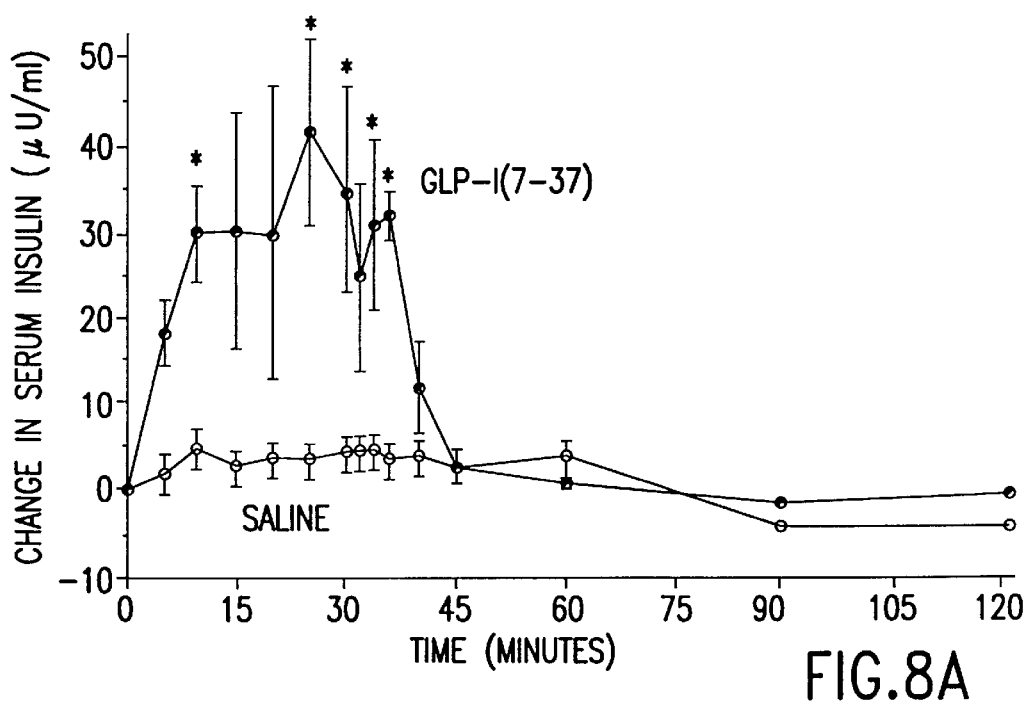

The fasted maturity onset diabetic subjects were found to respond to GLP-1(7-37) infusions (5 ng/kg/min) with relative insulin responses that were similar to those of the fasted non-diabetic subjects (FIG. 6). FIG. 8 depicts the absolute values of the data shown in FIG. 7. FIG. 7 shows relative percentage changes from the baseline (beginning of the infusion, time 0). FIGS. 7 and 8 show that infusion of GLP-1(7-37) (5 ng/kg/min) in three fasting non-insulin dependent diabetic subjects stimulates insulin secretion (bottom) and lowers plasma glucose levels (top). Results are expressed as change from baseline (plasma glucose 194±20 and 178±0.9 and 14.6±3.4 $\mu$U/ml at t=0 during placebo and GLP-1(7-37) infusion, respectively). Symbols are the same as in FIG. 6. The stimulation of insulin secretion is maintained throughout the 30 minute infusion of GLP-1(7-37). * denotes p<0.5 GLP-1(7-37) vs. placebo.

Table 10 shows the changes in insulin levels in both sets of subjects. (In Table 10, all values are expressed as mean±S.D.; * denotes peak insulin during 30 min infusion minus baseline (t=0) value; +denotes area under curve of insulin values between 0 and 30 minutes minus baseline insulin; # denotes only one NIDDM subject; @ denotes two NIDDM subjects; ++ denotes p<0.05 GLP-1(7-37) vs. saline infusion.) The basal, pre-GLP-1(7-37) infusion insulin levels of the maturity onset diabetic subjects were approximately 3-fold greater than were the levels of the non-diabetic subjects. GLP-1(7-37) infusions resulted in a graded insulin response with a similar 3-fold increase from pre-infusion levels as was observed for the non-diabetic subjects given the 5 ng/kg/min infusion. The insulin peak levels and insulin area under the curve increased by ten-fold compared with the values obtained during the placebo infusion of saline (Table 10). Unlike the responses in the non-diabetic subjects, the diabetic subjects experienced a more prolonged and variable period of increased insulin levels lasting until the termination of the GLP-1(7-37) infusion (FIGS. 7 and 8). Glucose levels of the diabetic subjects were in the clearly diabetic range at the beginning of the GLP-1(7-37) infusion (range 176–286 mg/dL, 9.78–15.9 mmol/L) and decreased progressively (range of 10% to 31% decrease from baseline) during the GLP-1(7-37) infusion and for a period of 30–90 minutes following termination of the infusion (FIGS. 7 and 8). GLP-1(7-37) infusions produced a graded increase in GLP-1(7-37) levels with a 1.5–3 fold increase during 2.5 to 5 ng/kg/min infusion rates, respectively, similar to the results obtained in the non-diabetic controls.

TABLE 10

Changes in Serum Insulin during Infusion of GLP-1(7-37) or Saline in Non-diabetic and NIDDM Subjects

|  | GLP-1(7-37) Infusion (ng/kg/min) | | | | |
| --- | --- | --- | --- | --- | --- |
|  | 0 (Saline) | 1.25 | 2.5 | 5.0 | 20.0 |
| Non-diabetic Subjects (n = 3) | 0 | — | — | 11.8 ± 6.7 | — |
| Peak Insulin (uU/mL)* | 0 | — | — | 219.0 ± 76.0 | — |
| NIDDM Subjects |  |  |  |  |  |
| Fasting studies (n = 3) |  |  |  |  |  |
| Peak insulin (uU/mL) | 5.0 ± 2.6 | 6.2# | 24 ± 15++ | 43 ± 21++ | 51 ± 18∂ |
| Area under curve | 123.0 ± 100 | 123.0# | 545 ± 422++ | 924 ± 571++ | 628 ± 317 |
| Meal Studies (n = 5) |  |  |  |  |  |
| Peak Insulin (uU/mL) | 10.0 ± 12.0 |  |  | 45 ± 6++ |  |
| Area under curve (uU/mL 30 min) | 141.0 ± 147 |  |  | 752 ± 535++ |  |

All values expressed as mean ± S.D.
*Peak insulin during 30 min infusion minus baseline (t = 0) value
+ Area under curve of insulin values between 0 and 30 minutes minus baseline insulin
Only one NIDDM subject
∂ Two NIDDM subjects
++ p < .05 GLP-1(7-37) vs. saline infusion Although the purpose of these studies was not to generate detailed and rigorous dose-response curves, it is apparent from the results that in the diabetic subjects, in whom several doses of GLP-1(7-37) were tested, there is a dose-related response for insulin secretion (Table 10) and to a modest extent for lowering of glucose levels. Responses were somewhat heterogeneous in that in one subject insulin secretion appeared to be maximal at the lowest dose of GLP-1(7-37) administered (2.5 ng/mg/kg).

Figure 7A:
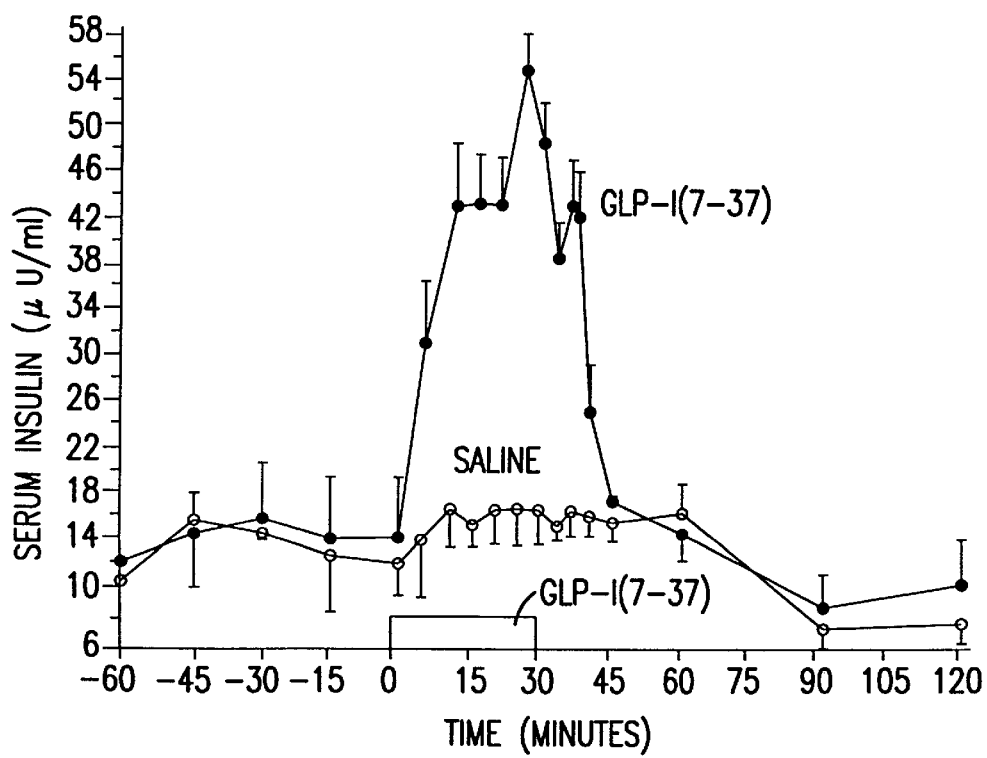

The achievement of near-steady state levels of GLP-1(7-37) during the 30-minute infusions permitted an estimation of the metabolic clearance rates (MCR) of the peptide (Table 11). The data for non-diabetic and diabetic subjects alike are in reasonably good agreement (MCRs of 14.6±1.7 and 12.4±2.9 ml/min/kg, respectively). Half-times of disappearance of the GLP-1(7-37) for non-diabetic subjects (9.7±1.9) and diabetic subjects (11.9±4.4 min) calculated from the equilibrium kinetics of the infusions were approximately 50% longer than the values of 6 minutes measured directly from the peptide decay curves following termination of the infusions (FIGS. 6 and 7 and 7A). No differences were observed in the MCRs or $T_{1/2}$'samongst the non-diabetic and diabetic subjects.

TABLE 11

GLP-1(7-37) Metabolic Clearance Rates in Non-diabetic and Diabetic Subjects

| Subjects | # | Weight (kg) | Infusion Rate (ng/kg/min) | Plasma** IR GLP-1 (ng/ml) | MCR (ml/min/kg) | T 1/2*** (min) |
| --- | --- | --- | --- | --- | --- | --- |
| Non-diabetic | 1 | 68 | 5 | 0.31 | 16.1 | 8.7 |
| Subjects | 2 | 82 | 5 | 0.43 | 11.6 | 11.9 |
|  | 3 | 70 | 5 | 0.31 | 16.1 | 8.5 |
|  | MEAN (SD) |  |  |  | 14.6 | 9.7 |
|  |  |  |  |  | (2.6) | (1.9) |
| Maturity Onset | 1 | 72 | 2.5 | 0.19 | 13.1 | 10.5 |
| Diabetic |  |  | 5.0 | 0.44 | 11.4 | 12.1 |
| Subjects |  |  | 20.0 | 3.3 | 6.1 | 23.1 |
|  | 2 | 70 | 2.5 | 0.18 | 13.9 | 9.1 |
|  |  |  | 5.0 | 0.49 | 10.2 | 13.5 |
|  |  |  | 20.0 | 1.5 | 13.3 | 10.3 |
|  | 3 | 81 | 1.25 | 0.09 | 14.7 | 9.4 |
|  |  |  | 2.5 | 0.16 | 15.6 | 8.9 |
|  |  |  | 5.0 | 0.37 | 13.6 | 10.2 |
|  | Mean (SD) |  |  |  | 12.4 | 11.9 |
|  |  |  |  |  | (2.9) | (4.4) |

*GLP-1(7-37) infused for 30 minutes.
**Difference between baseline and equilibrium values (achieved by 15–20 min of infusion)
***Calculated from steady-state equiaton assuming dH/dt = 0 and volume of distribution is the ECF (of body weight)

2) Results of Meal Studies.

Figure 9:
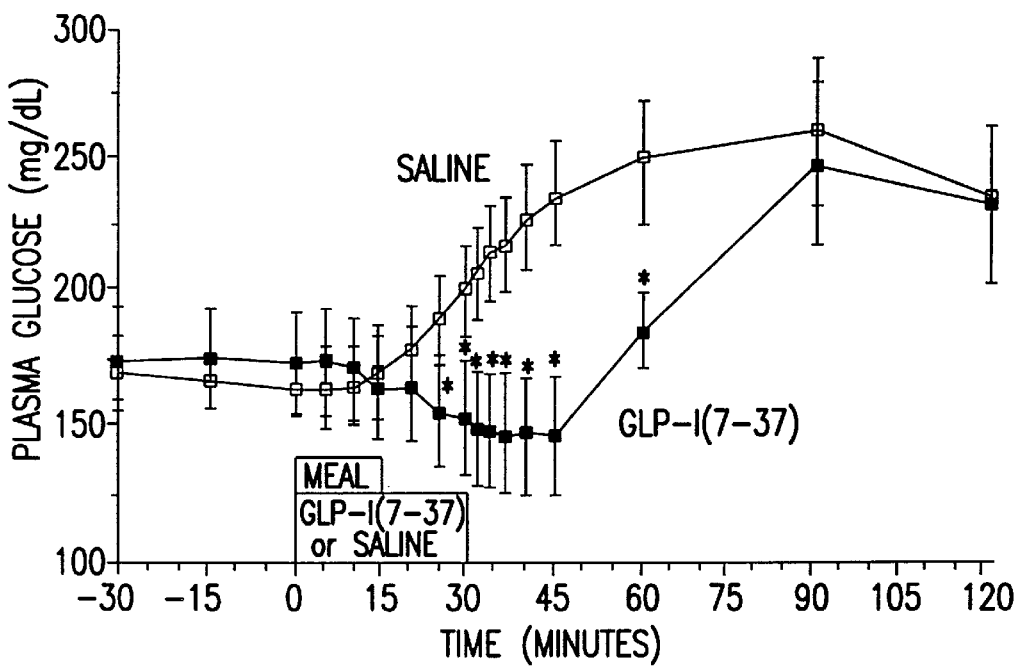
FIGS. 9 and 9A shows plasma glucose levels and serum insulin levels in maturity onset diabetic subjects during infusion of GLP-1(7-37) concurrent with a standard meal.

FIG. 9 shows the results of infusions of GLP-1(7-37) (5 ng/kg/min) in five non-insulin dependent diabetic subjects concurrent with a standard meal (closed squares and circles)

or infusion of a saline placebo (open squares and circles). Glucose results are in the top figure and insulin results are in the bottom figure. Symbols are the same as in FIG. 6. * denotes p<0.05 or GLP-1(7-37) vs. placebo.

Figure 9A:
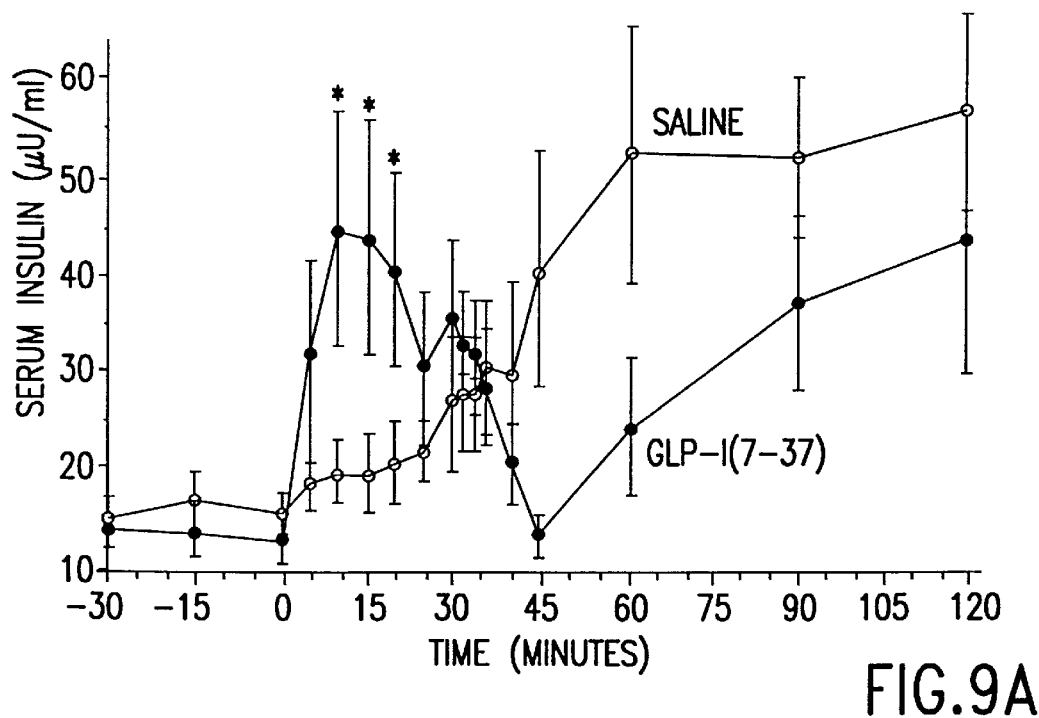

These studies showed uniform results among the five subjects. During GLP-1(7-37) infusion (5 ng/kg/min), the expected postprandial rise in plasma glucose was essentially eliminated for the first 60 minutes after the meal in association with a significant, three-fold increase in insulin levels compared with the placebo infusion (FIGS. 9 and 9A, Table 10). Mean plasma glucose fell from 174±44 mg/dL at the start of the meal and GLP-1(7-37) infusion to a nadir of 147±52 mg/dL 45 minutes later. With placebo infusion, plasma glucose increased from 164±25 mg/dL to 238±46 mg/dL during the same time period. The glucose level increased after cessation of the GLP-1(7-37) infusion and reached the same levels as with the placebo infusion by 120 minutes after the meal. Mean insulin level peaked 10 minutes after beginning the GLP-1(7-37) infusion and decreased during the remainder of the infusion, albeit remaining two-fold over baseline, similar to the pattern seen in the fasting studies in the non-diabetic subjects.

The single meal study in a non-diabetic was similar to the studies in the diabetic subjects showing a two-fold increase in insulin during GLP-1(7-37) infusion.

These results establish that GLP-1(7-37) stimulates insulin secretion in human subjects, including subjects with type II diabetes mellitus (maturity onset diabetes). The insulinotropic actions of GLP-1(7-37) appeared to be near maximal at doses of 2.5 to 5.0 ng/kg/min given for 30 minutes, infusion rates that raise the blood level of immunoreactive GLP-1(7-37) to approximately 1.5 to 2.5-fold of background levels. In the one subject to whom an infusion of 1.25 ng/kg/min was administered, a 1.5-fold rise in serum insulin levels was seen in circumstances in which no rise in circulating GLP-1(7-37) was detectable.

The meal studies demonstrate a similar insulinotropic effect of GLP-1(7-37) as seen in the fasting studies. Insulin levels associated with GLP-1(7-37) infusion led to a decrease in glucose levels post-prandially. Thus, in humans as well as in rats, GLP-1(7-37) is a physiologically potent stimulator of insulin secretion.

3) Glucose Dependence Studies

Figure 10:
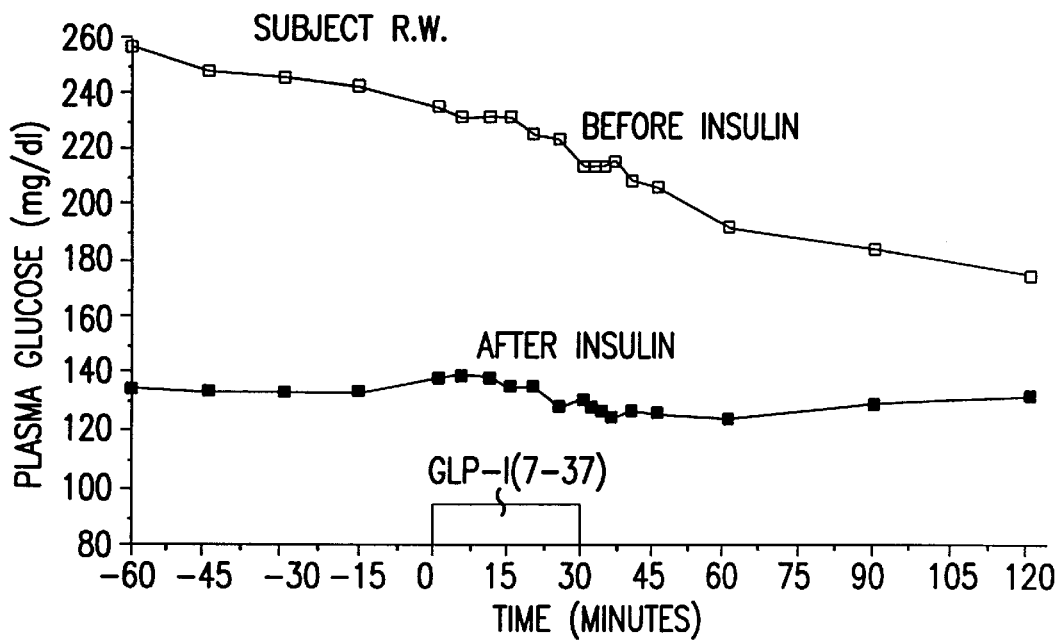

In the perfused rat pancreas and hamster and mouse insulinoma cell lines, the insulinotropic actions of GLP-1 (7-37) are glucose-dependent, that is, the insulinotropic actions are augmented by higher ambient glucose concentrations and attenuated by lower glucose concentrations. To determine whether, in the pancreas of human subjects, the insulinotropic actions of GLP-1(7-37) are also glucose dependent, the relative insulinotropic responses of GLP-1 (7-37) were studied in two subjects with type II diabetes mellitus before and after lowering their fasting glucose levels by the administration of an overnight insulin infusion. FIG. 10 shows the results of this study and the demonstration that the insulinotropic action of GLP-1(7-37) is glucose-dependent.

Figure 10A:
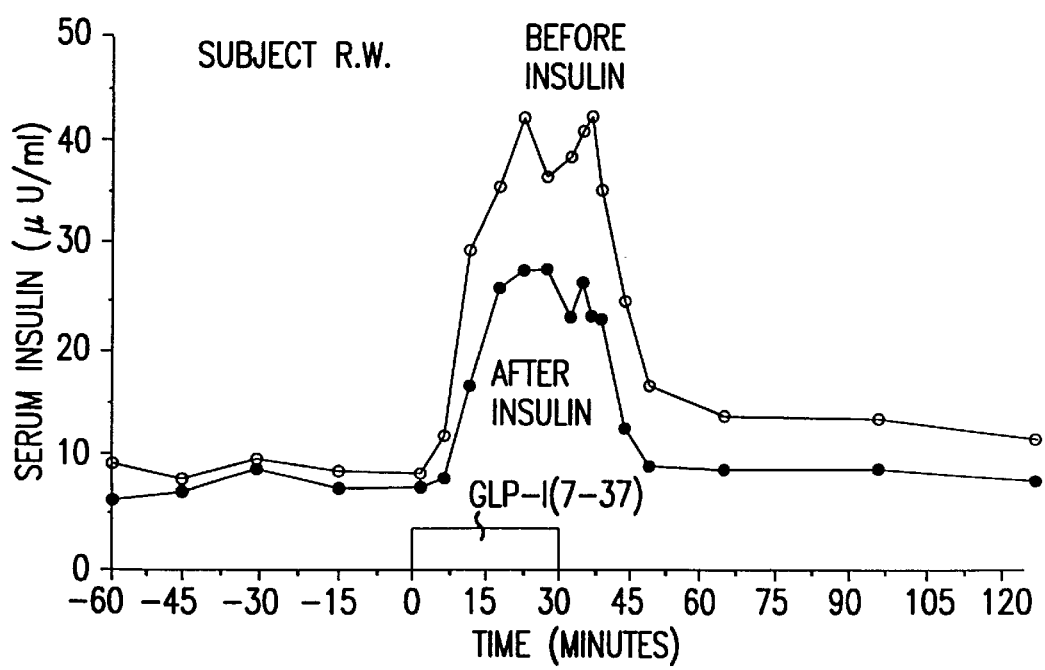
Figure 10B:
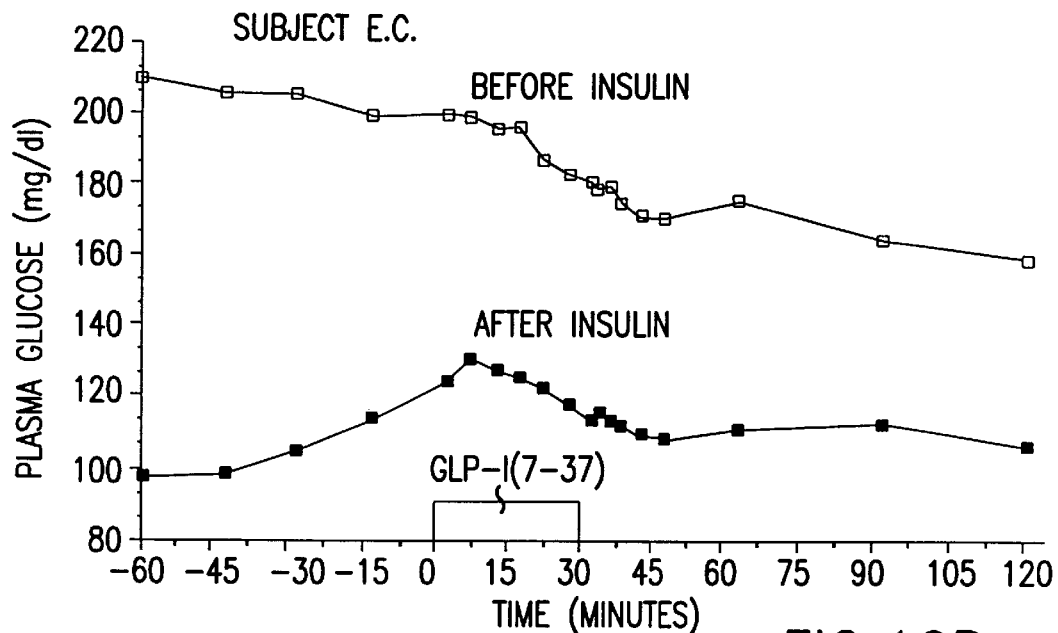
Figure 10C:
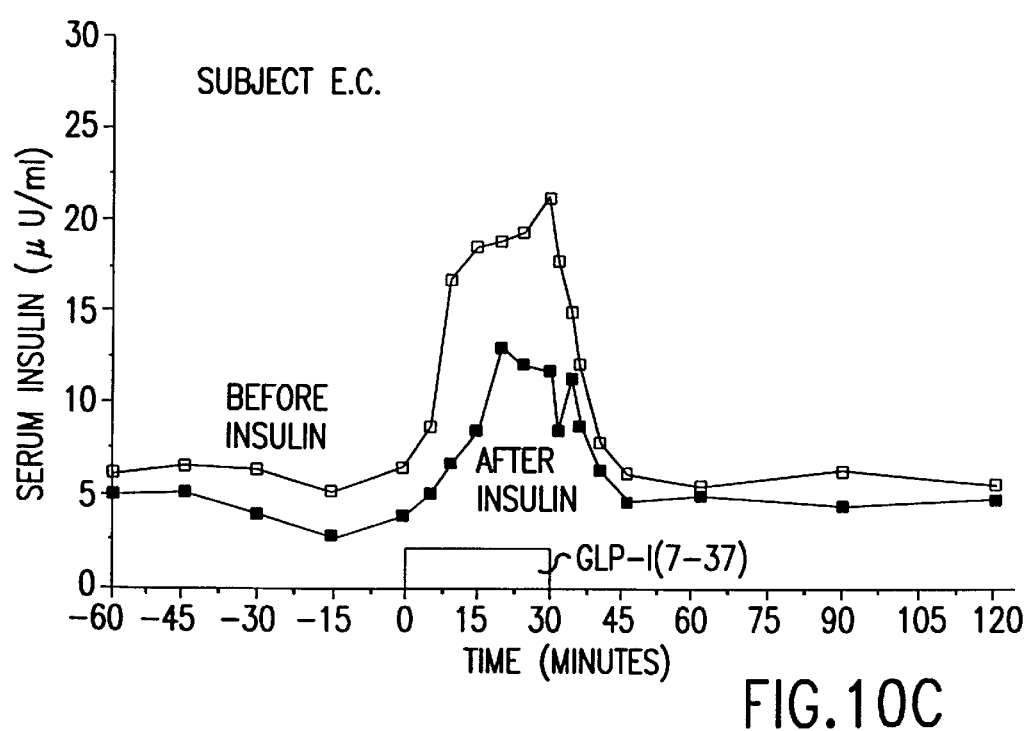

Two fasting subjects with hype II diabetes mellitus were administered a 30 minute infusion of GLP-1(7-37) at a dose of 5 ng/kg/min according to the precise protocol described for FIG. 7. During the night following the initial GLP-1(7-37) infusion (before insulin, open circles), the subjects were administered insulin to lower fasting plasma glucose levels. The following morning the insulin infusions were discontinued and additional GLP-1(7-37) infusion tests were carried out (after insulin, closed circles). The overnight insulin infusion resulted in a lowering of the fasting glucose levels in the two subjects from 236 mg/dL and 201 mg/dL (control day) to 124 and 133 mg/dL, respectively (after overnight insulin infusion (FIGS. 10(A) and (B))). The peak increments in insulin were 34 and 15 $\mu$U/ml in the two subjects in the first control GLP-1(7-37) infusion study. However, after the insulin infusion resulted in lower fasting glucose levels, GLP-1(7-37) infusion resulted in blunted GLP-1(7-37)-stimulated peak insulin increments of 20 and 8 $\mu$U/ml/ 30 min in the two subjects, respectively (FIGS. 10(A) and (B)). Thus, the results of these studies in two human subjects agree with the previously demonstrated direct glucose-dependency of the insulinotropic actions of GLP-1(7-37) in rat and mouse pancreatic beta cells. In addition, these results further support the utility of treating hyperglycemia, or hyperglycemic states, with GLP-1(7-37) administration.

In summary, the (1) demonstration that GLP-1(7-37) stimulated insulin secretion from the pancreas in subjects with type II diabetes mellitus, coupled with (2) the results of experiments presented in the examples that demonstrate the in vitro insulinotropic properties all GLP-1(7-37) and GLP-1(7-36), support a conclusion that GLP-1(7-36) in addition to GLP-1(7-37), has utility as a therapeutic agent for the treatment of maturity onset diabetes.

It is desirable to treat patients with type II diabetes mellitus with an agent that stimulates endogenous insulin secretion rather than administering insulin by subcutaneous injections because the endogenous insulin is delivered directly to the liver through the portal blood flow rather than from the systemic circulation. Furthermore, in vivo GLP-1appears to be produced almost entirely in the intestinal neuroendocrine L-cells and released into the bloodstream in response to the ingestion of oral nutrients. Thus, GLP-1(7-37) and its derivatives, unlike the sulfonylureas, is a naturally occurring substance that could be exploited as an effective medication for the treatment of type II diabetes mellitus. It is a significant advantage of the invention that, because of the postulated direct dependency of the insulinotropic actions of GLP-1(7-37) on the glucose levels demonstrated in vitro (Weir et al., *Diabetes* 38:338–342 (1989)), hypoglycemia, as occurs in the treatment of patients with subcutaneously administered insulin or oral sulfonylureas, predictably would not be a side-effect of treatment with GLP-1(7-37).

The results presented above demonstrate that GLP-1(7-37) stimulates insulin secretion and lowers plasma glucose levels, in these patients, at infusion rates of peptide (1–5 ng/kg/min over 30 min) that raise plasma levels of immunoreactive GLP-1(7-37) by only 0.5 to 2-fold. The results indicate that insulinotropic activity was demonstrable with a 30-minute infusion in both the fasting state and when administered concurrent with a meal. In diabetic subjects, GLP-1(7-37) infusion (compared with placebo) was found to lead to a three-fold increase in insulin levels and completely eliminated the post-prandial rise in plasma glucose for 60 min after beginning the meal.

These studies present evidence of the potent insulinotropic effects of GLP-1(7-37) in patients with noninsulin-dependent (type II) diabetes mellitus as well as in non-diabetic subjects. These findings of potent insulinotropic actions of GLP-1(7-37) in patients with type II diabetes in both the fasting and prandial states indicate that GLP-1(7-37) and its derivatives GLP-1(7-35) and GLP-1(7-34) have therapeutic utility as an effective medication for the treatment of patients with hyperglycemia or type II diabetes mellitus (maturity onset diabetes).

Example 12

Insulinotropic Hormone GLP-1(7-37) Stimulation of Proinsulin Gene Expression and Proinsulin Biosynthesis in Insulinoma Cells During the intestinal processing of proglucagon, two bioactive forms of GLP-1are synthesized (Mojsov et al., *J.*

Biol. Chem. 265:8001–8008 (1990)): GLP-1(7-37) and GLP-1(7-36)amide; it has been discovered that both peptides possess identical insulin releasing effects. Since the N-terminal part of the molecule is responsible for receptor binding and activation the biological importance of the existence of these forms of GLP-1is unknown. Therefore, with regard to function, at the pancreatic B-cell, GLP-1(7-37) and GLP-1(7-36) amide can be used synonymously.

This study characterizes GLP-1(7-37) as a stimulator of proinsulin gene transcription and biosynthesis in the glucose-responsive mouse insulinoma cell line βTC-1. These studies lead to a concept that GLP-1(7-37) represents not only a physiologically important insulin secretagogue but also replenishes insulin in the β-cell by increasing proinsulin gene transcription and biosynthesis.

To study the mechanism by which GLP-1(7-37) might act on proinsulin gene transcription, gel mobility shift assays were performed using synthetic oligonucleotides containing the sequence for the CRE (cyclic AMP response element) of the rat insulin I gene, nuclear extracts from βTC-1 cells and bacterial CREB (cyclic AMP response element binding protein) 327/341.

I. METHODS

A. Cell Culture

βTC-1 cells (Efrat et al., *Proc. Natl. Acad. Sci. (USA)* 85:9037–9041 (1988)) were grown in a humidified atmosphere at 37° C. in RPMI 1640 medium supplemented with 10% (vol/vol) fetal bovine serum, 5% (vol/vol) horse serum, 100 U/ml penicillin and 100 μg/ml streptomycin. Media were changed after three days and cells were split 1:3 after six days.

B. Cell Transfections and CAT-assay

Cells of two 80–90% confluent 150 mm culture plates were trypsinized and transfected in solution in one tube with 15 μg of indicator plasmid using the DEAE-dextran method. The plasmid contained 410 bp of the rat insulin I gene promoter fused to the transcriptional reporter gene encoding the bacterial enzyme chloramphenicol-acetyltransferase (CAT). The plasmid was constructed by linking the Pvu II/RsaI fragment (−140 to +65) of the rat insulin I gene into the vector PO-CAT. Subsequently cells were plated into 18 wells of six well plates. This procedure provides parallel experimental and control cells from the same transfection at identical conditions (the same media changes, harvest at identical time points, with or without treatments with GLP-1(7-37) or signal transducing agents). The cell number of each well was controlled by determination of protein concentration in the cell lysate and did not vary by more than 10%. Thereby, differences in transfection deficiencies reflected in CAT activities were normalized against protein concentrations as well as the respective control experiments. After transfection cells were incubated in RPMI 1640 supplemented with 0.1% human serum albumin and 0.1% bacitracin. Treatment of cells was begun immediately after transfection and the respective agents were added from 100×stock solutions [(GLP-1(7-37); IBMX; 8-Bromo-cAMP; or 1000×stock solution (forskolin). After 24 hours incubation under these conditions cells were harvested in 1.5 ml buffer containing 150 mM NaCl, 1 mM EDTA and 40 mM Tris/Cl pH 7.4 and lysed in 70 μl 1M Tris/Cl pH 7.4 by three freeze-thaw cycles. CAT activities were determined in 55 μl of cell lysates; the assay mixture was 70 μl 1M Tris/Cl pH 7.4, 55 μl cell lysate in 250 mM Tris/Cl pH 7.4, 20 μl 4 mM acetyl-CoA in water, 0.5 μl $^{14}$C chloramphenicol (0.05 μCi) and incubations were carried out for 120 minutes. After extraction with ethylacetate (1 ml) acetylated and non-acetylated $^{14}$C-chloramphenicol were separated by thin-layer chromatography (chloroform:methanol 9:1), identified by autoradiography and the respective spots were scraped from the plates and radioactivity was counted in a scintillation counter.

C. Studies of Proinsulin Biosynthesis

βTC-1 cells were plated into 35 mm plates and grown for two days to reach 80–90% confluency. During a 6 hour labeling period cells were incubated in 1 ml RPMI 1640 supplemented with 0.1% human serum albumin, 0.1% bacitracin and 50 μCi[$^3$H]leucine. Forskolin, IBMX, 8-Bromo-cAMP and GLP-1(7-37) were added from stock solutions as described (see "cell transfection"). Cells were harvested in PBS and lysed by three freeze-thaw cycles. Immunoreactive proinsulin was precipitated with an antiserum raised in rabbits against pork insulin that was coupled to a 10% suspension of bacterial lysates (Saureus) containing protein A. Radioactivity contained in the resulting pellets was counted using a liquid scintillation counter. Incorporation of [$^3$H]leucine into total protein was measured in trichloroacetic acid precipitates of the cells. None of the agents tested had any effects on [$^3$H]leucine incorporation into TCA precipitable proteins. Data are expressed as fold-induction of proinsulin biosynthesis above those in the control experiments (no treatment).

D. Determination of Cellular Insulin Content

Two days before the experiment commenced, cells were plated into 35 mm plates. Media were changed to RPMI 1640 supplemented with 0.1% human serum albumin and 0.1% bacitracin. Forskolin, IBMX, 8-Bromo-cAMP and GLP-1(7-37) were added as described (see "cell transfections"). After incubation for 24 hours under these conditions, cells were washed three times with PBS and harvested in 1.5 ml buffer containing 150 mM NaCl, 1 mM EDTA and 40 mM Tris/Cl pH 7.4 and resuspended in 200 μl PBS. Fifty μl of this cell suspension were resuspended in 1 ml 1 M acetic acid and extracted for 16 hours at 4° C. . Aliquots (2 and 20 μl) were lyophilized and reconstituted in insulin-RIA buffer. The cell number of each plate was controlled by determination of total protein in the initial cell lysate. Protein concentrations did not vary more than 10%. Insulin was measured with a radioimmunoassay system using an antiserum raised in rabbits against pork insulin and pork insulin as the standard. Free and bound hormones were separated by dextran-coated charcoal (Albano et al., *Acta Endocrinol. (Copehn.)* 70:487–494 (1972)). Data are presented as fold-increase of insulin content per well above the control experiments (no treatment).

II. RESULTS

Figure 11:
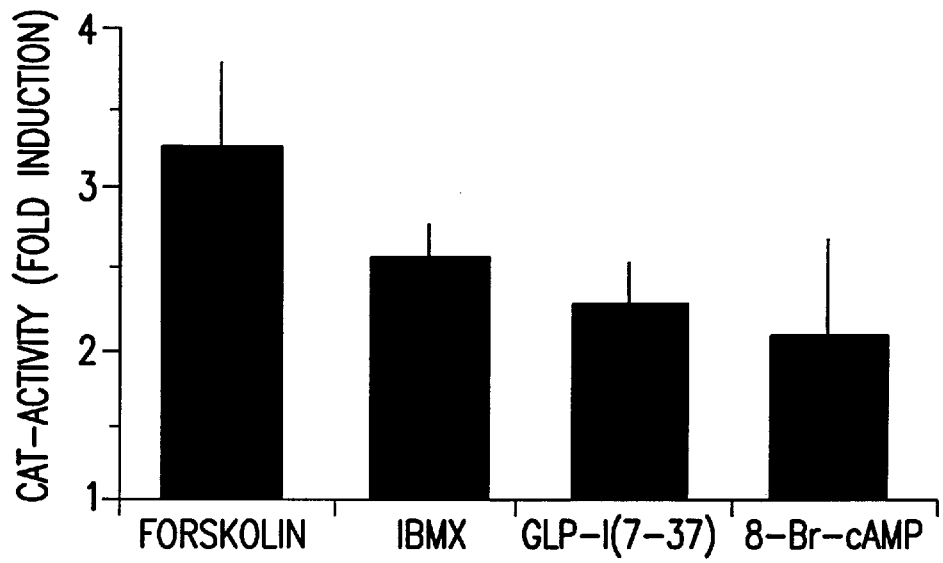
FIG. 11 shows induction of CAT-activity by forskolin (10 μM), IBMX (0.5 mM), 8-Bromo-cAMP (1 mM) and GLP-1(7-37) (10 nM) in transient transfected βTC-1 cells, treated for 24 hours. Mean±S.D. of or 4 experiments, each performed in triplicate.

A. Transfection Experiments

βTC-1 cells were transiently transfected with a plasmid containing 410 bp of the rat insulin I gene promoter fused to the transcriptional reporter gene encoding the bacterial enzyme chloramphenieol-acetyltansferase. Cells were treated for 24 hours with forskolin, IBMX, 8-Bromo-cAMP and GLP-1(7-37) as indicated and CAT-activities in the cell lysates were determined. GLP-1(7-37) (10 nM) induced a 2.3±0.23 fold increase of CAT activity compared to control cells (no treatment) (FIG. 11). Forskolin (10 μM), IBMX (0.5 mMo and 8-Bromo-cAMP (1 mM) increased CAT activity 3.3±0.57, 2.6±0.16 and 2.1±0.8 fold, respectively.

Figure 12:
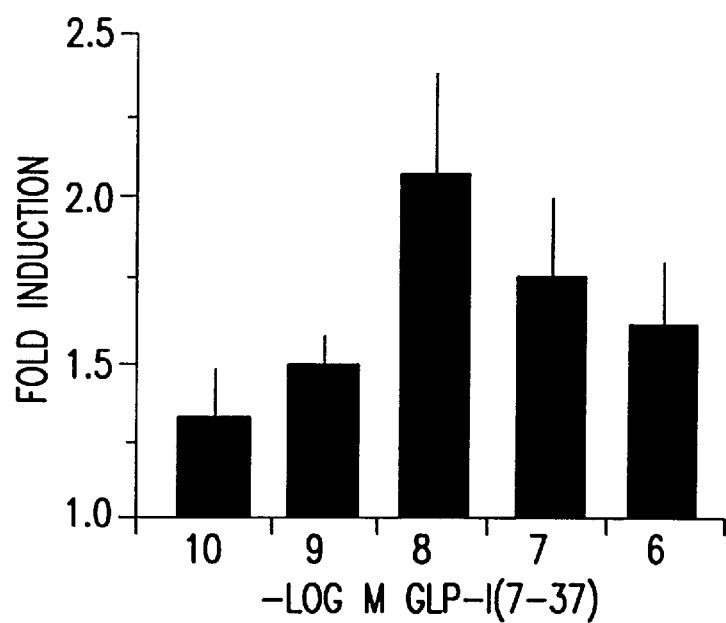
FIG. 12 shows induction of CAT-activity by increasing concentrations of GLP-1(7-37) in βTC-1 cells transient transfected for 24 hours with the −410 Ins-CAT expression plasmid. Mean±S.D. of 3 or 4 experiments, each performed in triplicate.

In the next set of experiments transiently transfected βTC-1 cells were treated with increasing concentrations of GLP-1(7-37) (100 pM-1 μM) (FIG. 12). The GLP-1(7-37) effect was maximal at 10 nM (2.1±0.3 fold induction) and in cells treated with 0.1 and 1 μM GLP-1(7-37) CAT-activity was clearly lower compared to cells exposed to 10 nM GLP-1(7-37).

B. Proinsulin Biosynthesis Experiments

Figure 13:
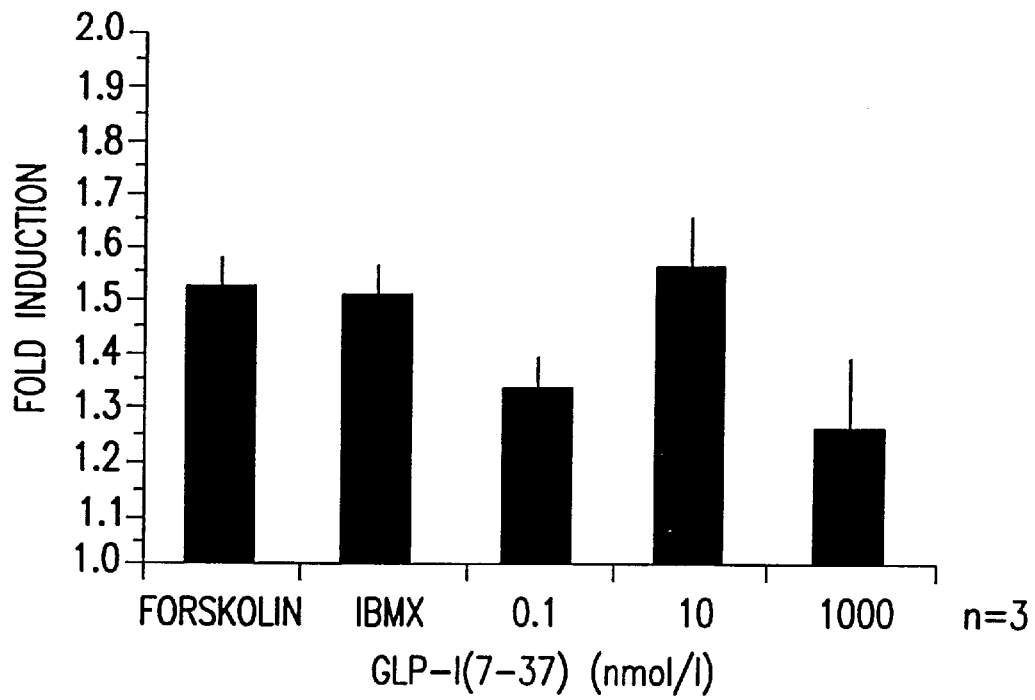
FIG. 13 shows induction of proinsulin biosynthesis in βTX-1 cells by forskolin (10 μM), IBMX (0.5 mM) and GLP-1(7-37) (0.1, 10, 1000 nM) during a 6 hour labelling and stimulating period. Mean±S.D. of 3 or 4 experiments, each performed in triplicate.

During the 6 hours of labeling of βTC-1 cells with [³H]leucine, forskolin (10 μM) and IBMX (0.5 mM) induced a 1.53±0.06 fold increase of proinsulin biosynthesis (FIG. 13). Comparable to the transfection experiments, GLP-1(7-37) stimulated proinsulin biosynthesis concentration-dependently with a maximal action at 10 nM (1.56±0.11-fold increase). At 1 μM GLP-1(7-37), ³H-incorporation into proinsulin was lower (1.26±0.13 fold increase) compared to the experiments with 10 nM GLP-1(7-37) (FIG. 13).

C. Effect of GLP-1(7-37) on Insulin Content in βTC-1 cells

Figure 14:
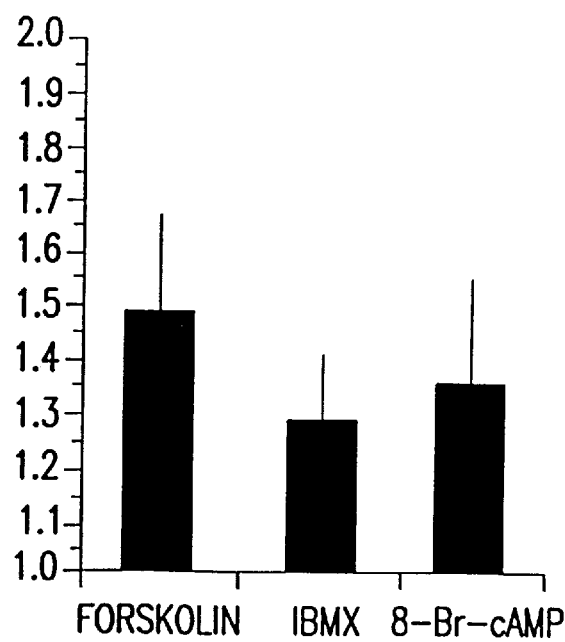
FIG. 14A shows increase of proinsulin content in βTC-1 cells after 24 hour treatment with forskolin (10 μM), IBMX (0.5 mM) and 8-Bromo-cAMP (1 mM). Mean±S.D. of 3 experiments, each performed in triplicate.
FIG. 14B shows increase of proinsulin content in βTC-1 cells after treatment with GLP-(7-37) (0.1–100 nM). Mean±S.D. of 3 experiments, each performed in triplicate.
Figure 14A:
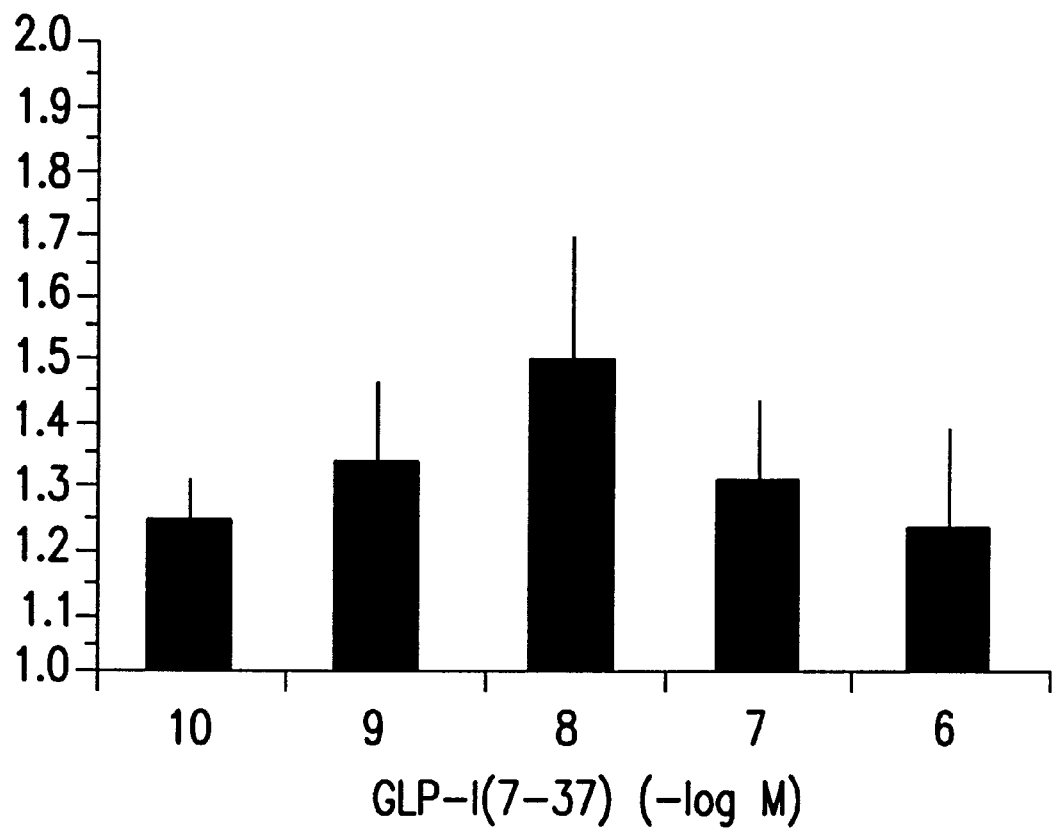

Treatment of βTC-1 cells for 24 hours with forskolin (10 μM), IBMX (0.5 mM), and 8-Bromo-cAMP (1 mM), induced an increase of total cellular insulin content (1.49±0.18, 1.30±0.12 and 1.36±0.28 fold-increase) (FIG. 14A). The increase of total cellular insulin content induced by GLP-1(7-37) was maximal at 10 nM GLP-1(7-37) (1.52±0.20 fold increase) and cells treated with 0.1 and 1 μM GLP-1(7-37) contained less insulin compared to cells exposed to 10 nM GLP-1(7-37) (1.33±0.11 and 1.26±0.21 fold increase) (FIG. 14B).

D. Binding of Nuclear Factors and CREB 327/341 to the Insulin Gene CRE

Gel-shift analysis was done in order to study nuclear proteins from βTC-1 cells binding to the rat insulin I gene. Cyclic response element nuclear extracts from these cells were prepared, incubated with a labeled double-stranded synthetic oligonucleotide containing the sequence of 195 to −170 of the rat insulin I gene promoter and bacterially expressed CREB 327/341. The DNA/protein complexes were separated by electrophoresis. Sample 1 contained free probe. Samples 2–4 contained CREB 327/341 and a 1000, 100, and 10-fold molar excess of unlabeled oligonucleotide. Sample 5 contained CREB 327/341, but no specific competitor was added. Two proteins with different affinities to the insulin gene CRE could be identified. Binding of the protein with the lower electrophoretic mobility to this gene fragment was partially competed by the addition of a 10-fold molar excess of unlabeled oligonucleotide and 100 and 1000-fold molar excess abolished the binding completely. Binding of the protein with the higher electrophoretic mobility was partially competed only by a 1000-fold molar excess of unlabeled oligonucleotide. Because it seemed possible that one of the detected insulin CRE binding proteins represents CREB, the possibility was investigated whether bacterial CREB 327/341 binds in vitro to this gene fragment.

Gel-shift analysis of nuclear extracts from βTC-1 cells was done using a labeled double-stranded synthetic oligonucleotide containing the sequence of 195 to −170 of the rat insulin I gene promoter. Sample 1: free probe; Sample 2: nuclear extracts, but no specific competitor added; Samples 3–5: nuclear extracts, and a 10-, 100- and 1000-fold molar excess of unlabeled oligonucleotide added. The results showed that this bacteria] expressed protein (CREB 327/341) binds in vitro specifically to the insulin gene CRE. The binding was competed concentration-dependently and comparable to the protein with the lower electrophoretic mobility detected in βTC-1 cell nuclear extracts. Even a 10-fold molar excess of unlabeled oligonucleotide inhibited the binding of this protein to the labeled probe.

E. Detection of CREB 327/341 in Nuclear Extracts of βTC-12 Cells

To test the possibility of whether βTC-1 cells express CREB 327/341-like proteins, nuclear proteins of these cells were separated by SDS polyacrylamide gel electrophoresis and blotted on nitrocellulose. Using the Western blot technique and a specific antiserum directed against CREB 327/341, a single band was detected representing a protein of approximately 40 kD that ran in parallel with bacterially-expressed CREB 327/341.

III. DISCUSSION

Figure 15:
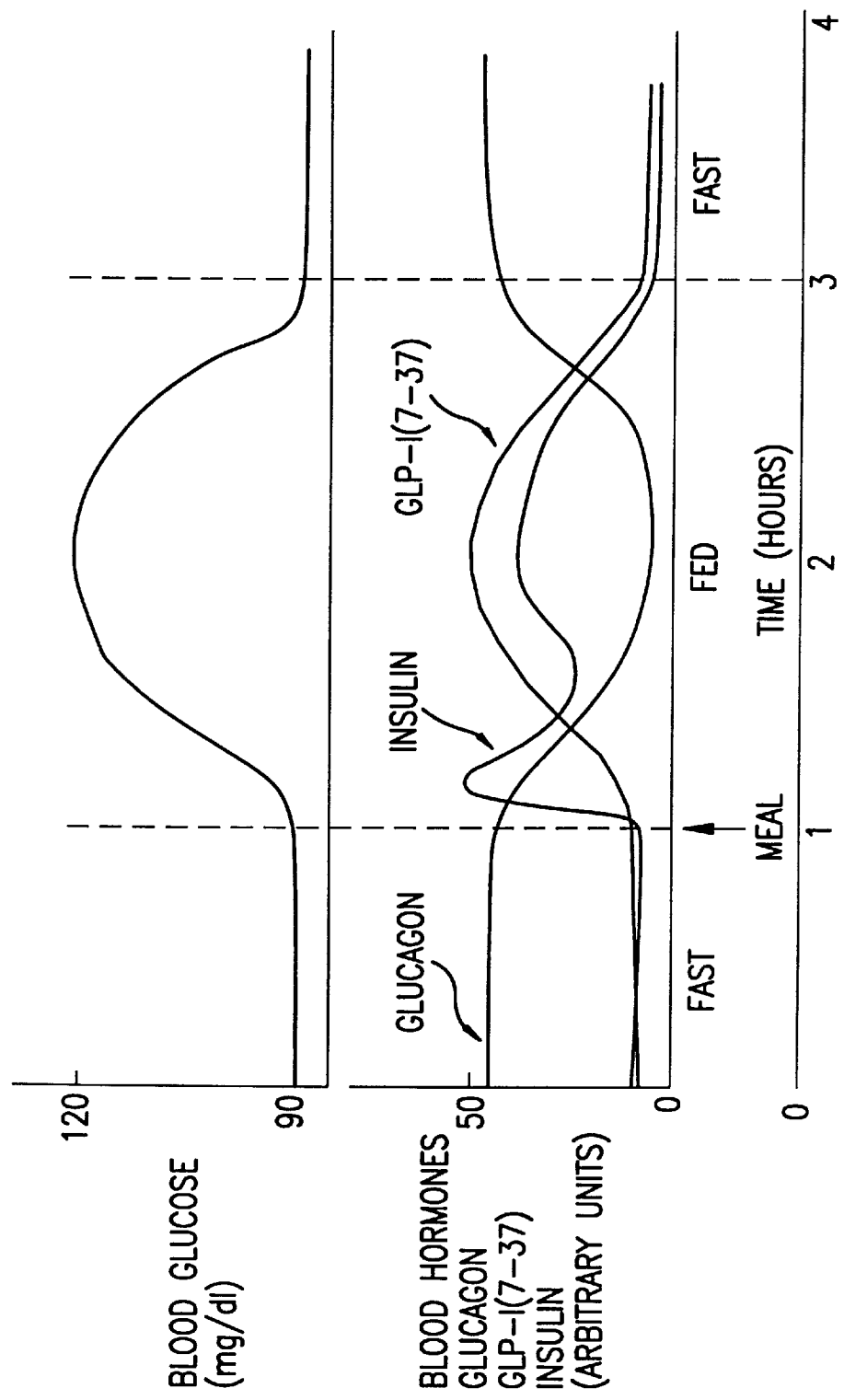
FIG. 15 shows a diagrammatic depiction of the changes in blood glucose and hormone levels during fasting and feeding in animals and humans. It is important to note that glucagon levels rise during fasting in order to stimulate the liver to synthesize glucose to maintain blood glucose levels at 90 mg/dl. During fasting insulin and GLP-1(7-37) levels are low. The secretion of the latter two hormones is stimulated by feeding so that insulin can act on peripheral organs to take up and assimilate glucose and other meal-derived nutrients.

The above study of Example 12 demonstrates that GLP-1(7-37) is a potent stimulator of proinsulin gene transcription and proinsulin biosynthesis that results in an elevated cellular content of insulin after treatment of insulinoma βTC-1 cells with GLP-1(7-37). Therefore, GLP-1(7-37) is not only a powerful insulin secretagogue but it also acts as an "insulinotropic" substance that restores the intracellular insulin pool via an increase of proinsulin gene transcription and biosynthesis. These properties discriminate GLP-1(7-37) from (1) other substances such as the sulphonylureas that act as potent insulin secretagogues but not as stimulators of proinsulin biosynthesis (Morris et al., *Biochim. Biophys. Acta* 208:404–413 (1970); Schatz et al., *Acta Endocrinol. (Copenh)* 26:237–240 (1972)), and (2) from other structurally related polypeptide members of the glucagon-related superfamily that do not share this insulinotropic property. The findings lead to a wider concept of the entero-insulinar axis in which GLP-1(7-37) releases insulin directly after GLP-1(7-37) is secreted from the intestine in response to a meal (FIG. 15). By elevating intracellular cAMP levels of B cells, transcriptional and probably translational mediators are activated, resulting in an increase in proinsulin biosynthesis during interprandial periods when the insulin secretory demand is low, thereby preparing the B cell for the next meal.

The actions of GLP-1(7-37) on proinsulin gene transcription were concentration-dependent with a maximum at 10 nmol/l. This observation correlates with earlier findings demonstrating a maximal stimulation of insulin release and cAMP generation from perfused and incubated insulinoma cells in the presence of 10 nM GLP-1(7-37) (Fehmann et al., *FEBS Let.* 279:335–340 (1991); Fehmann et al., *Endocrinology* 128 (in press) (1991)). The inhibition of insulin release and cAMP production at concentrations above 10 nmol/l GLP-1(7-37) was shown to be due to a rapid and reversible homologous desensitization of the GLP-1(7-37) receptor (Fehmann et al., *Endocrinology* 128 (in press) (1991)). This phenomenon might also account for the decrease in proinsulin gene transcription and proinsulin biosynthesis in the presence of 100 and 1000 nmol/l GLP-1(7-37). Other G-protein coupled receptors (e.g., β-adrenergic receptor, M1-muscarinergic receptor) were shown to be down-regulated by longer exposure of cells with high concentrations of ligands (Wang et al., *FEBS-Lett.* 276:185–188 (1990); Hausdorff et al., *Faseb J.* 4:2881–2889 (1990)). Therefore, a ligand-induced down-regulation of the GLP-1(7-37) receptor might also contribute to the decreased proinsulin gene transcription. Because this latter phenomenon appears to be regulated at least in part by the mRNA levels (Wang et al., *FEBS-Lett.* 276:185–188 (1990); Hausdorff et al., *Faseb J.* 4:2881–2889 (1990)), equivalent studies with the GLP-1(7-37) receptor can be performed after cloning and isolation of the cDNA encoding the GLP-1(7-37) receptor.

Of interest in this context is the recent finding of elevated GLP-1(7-37) levels in plasmas of patients with non-insulin dependent diabetes mellitus (NIDDM). Although not intending to be bound by this interpretation, it is possible that a homologous desensitization on the GLP-1(7-37) receptor might contribute to the impaired insulin secretion in this disorder (Orskov et al., *J. Clin. Invest.* 87:415–423 (1991)). In addition, it is possible that proinsulin gene transcription and proinsulin biosynthesis also might be decreased in patients with NIDDM. However, in vitro studies with insulinoma cells may not accurately reflect the in vivo pathophysiological situation in man.

The data are in agreement with studies demonstrating increased levels of proinsulin mRNA after treatment of islets or cultured B-cells with agents that elevate intracellular cAMP levels (Drucker et al., *Proc. Natl. Acad. Sci. (USA)* 84:3434–3438 (1987); Niesen et al., *J. Biol Chem.* 260:11585–11589 (1985); Welsh et al., *J. Biol. Chem.* 260:13590–13594 (1985); Hammonds et al., *FEBS-Lett.* 213:149–154 (1987); Hammonds et al., *FEBS-Lett.* 23:131–137 (1987); Philippe et al., *J. Biol. Chem.* 265:1465–1469 (1990); German et al., *J. Biol. Chem.* 265:22063–22066 (1990)). Results obtained in the transient transfection experiments support the concept that GLP-1(7-37) acts via cAMP-mediated proinsulin gene transcription (Philippe et al., *J. Biol Chem.* 265:1465–1469 (1990)). In addition, it was shown previously that both GIP and the cAMP analog dibutyxl cAMP stimulate proinsulin biosynthesis in pancreatic and cultured insulinoma (RINm5F) cells, respectively (Schäfer et al., *Acta Endocrinol. (Copenh)* 91:493–500 (1979); Dobs et al., *In Vitro Cell Dev. Biol.* 25:112–114 (1989)).

A recent report using HIT-T15 cells characterized a functionally active cAMP responsive element (CRE) in the promoter region (−184 to −176) of the rat insulin I gene (Philippe et al., *J. Biol. Chem.* 265:1465–1469 (1990)). Functional data, performed in another insulinoma cell line (TC-1 cells), confirm these and previous results obtained in studies with isolated islets from different species that demonstrate elevated levels of proinsulin mRNA after treatment with substances that increase intracellular cAMP levels (Drucker et al., *Proc. Natl. Acad. Sci. (USA)* 84:3434–3438 (1987); Niesen et al., *J. Biol. Chem.* 260:11585–11589 (1985); Welsh et al., *J. Biol. Chem.* 260:13590–13594 (1985); Hammonds et al., *FEBS-Lett.* 213:149–154 (1987); Hammonds et al., *FEBS-Lett.* 223:131–137 (1987); Philippe et al., *J. Biol. Chem.* 265:1465–1469 (1990); German wet al., *J. Biol. Chem.* 265:22063–22066 (1990)). Although not intending to be bound by this interpretation, these data suggest a model for a mechanism for the action of GLP1 (7-37) on proinsulin gene transcription: GLP-1(7-37) receptor binding activates the adenylate cyclase system that triggers an increased activity of protein kinase A that phosphorylates and activates CREB 327/341 (Lee et al., *EMBO J.* 9:4455–4465 (1990); Habener et al., *Mol. Endocrinol.* 4:1087–1094 (1990)).

Figure 16:
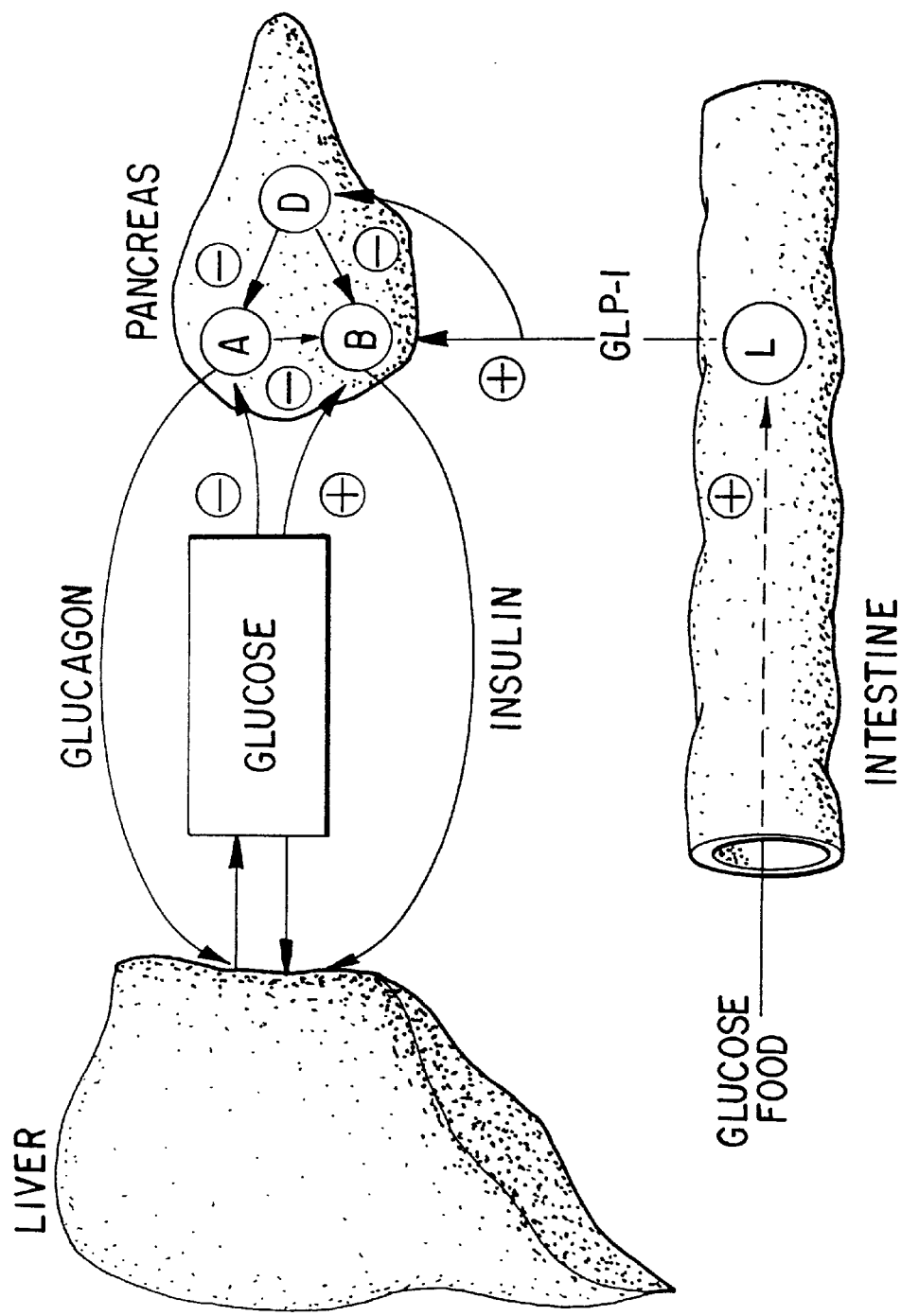
FIG. 16 shows a diagram of the insulinotropic actions of GLP-1(7-37). Oral nutrients, such as glucose, absorbed from the intestine during a meal stimulate the intestinal L-cells to secrete GLP-1(7-37) which in turn stimulates the pancreatic B-cells to produce insulin.

In conclusion, this study extends the knowledge of the entero-insulinar ("incretin") axis by demonstrating that GLP-1(7-37) stimulates proinsulin gene expression and proinsulin biosynthesis (FIG. 16). Although blood glucose and other nutrients, e.g. amino acids, are the major stimulants of insulin secretion, the secretory actions of the nutrients are markedly augmented by GLP-1(7-37) through its actions on specific receptors located on the B-cells. In contrast to the stimulation of insulin and GLP-1(7-37), the rise in blood glucose and nutrients following a meal suppresses the secretion of glucagon from the A-cells. Recently, it was discovered that the D-cells that produce somatostatin also have GLP-1(7-37) receptors raising the possibility of yet additional control mechanisms by which somatostatin may exert a paracrine negative feedback to suppress glucagon-secretion further and to dampen the insulinotropic actions of GLP-1(7-37).

GLP-1(7-37) represents not only an important mediator of postprandial insulin release, but also restores the insulin pool of the pancreatic B-cell. Therefore, GLP-1(7-37) is a real physiological "insulinotropin" and not only an "insulin-secretagogue." The action of GLP-1(7-37) on proinsulin gene transcription is likely to be mediated at least in part by the cAMP-responsive transcriptional transactivator protein CREB 327/341.

Having now fully described this invention, it will be apparent to one of ordinary skill in the art that the same may be carried out with minor modifications which do not affect the content or spirit thereof.

What is claimed is:

1. DNA encoding a fragment of GLP-1(1-37) and not the native GLP-1(1-37), wherein said fragment has the amino acid sequence: His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly, and wherein said native GLP-1(1-37) has the amino acid sequence: His-Asp-Glu-Phe-Glu-Arg-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala—Trp-Leu-Val-Lys-Gly-Arg-Gly.

2. The DNA of claim 1, consisting of the sequence: CATTGCTCAACGGGACCTTTACCAGT-GATGTGAGTTCTTACTTGGAGGGCCAGGCAGCA AAGGAATTCATTGCTTGGCTGGTGAAAG-GCCGAGGA.

* * * * *

UNITED STATES PATENT AND TRADEMARK OFFICE
CERTIFICATE OF CORRECTION

PATENT NO.   : 6,162,907
DATED        : December 19, 2000
INVENTOR(S)  : Joel F. Habener It is certified that error appears in the above-identified patent and that said Letters Patent is hereby corrected as shown below:

<u>Column 32,</u>
Lines 43-46, please delete
"CATTGCTCAACGGGACCTTTACCAGTGATGTGAGTTCTTACTTGGAGGGCCAGGCAGCAAAGGAATTCATTCATTGCTTGGCTGGTGAAAGGCCGAGGA"

and insert the following

-- CATGCTGAAGGGACCTTTACCAGTGATGTGAGTTCTTACTTGGAGGGCCAGGCAGCAAAGGAATTCATTGCTTGGCTGGTGAAAGGCCGAGGA --

Signed and Sealed this

Ninth Day of April, 2002

Attest:

*Attesting Officer*

JAMES E. ROGAN
*Director of the United States Patent and Trademark Office*